United States Patent
Peterson

(10) Patent No.: US 7,565,248 B2
(45) Date of Patent: Jul. 21, 2009

(54) COMPUTER SYSTEM FOR DESIGNING OLIGONUCLEOTIDES USED IN BIOCHEMICAL METHODS

(75) Inventor: Raymond J. Peterson, Greenbelt, MD (US)

(73) Assignee: Celadon Laboratories, Inc., College Park, MD (US)

( * ) Notice: Subject to any disclaimer, the term of this patent is extended or adjusted under 35 U.S.C. 154(b) by 215 days.

(21) Appl. No.: 10/398,445

(22) PCT Filed: Oct. 4, 2001

(86) PCT No.: PCT/US01/31037

§ 371 (c)(1),
(2), (4) Date: Jan. 23, 2004

(87) PCT Pub. No.: WO02/29379

PCT Pub. Date: Apr. 11, 2002

(65) Prior Publication Data

US 2004/0166498 A1    Aug. 26, 2004

Related U.S. Application Data

(60) Provisional application No. 60/237,383, filed on Oct. 4, 2000.

(51) Int. Cl.
*G06F 19/00*    (2006.01)
*C12Q 1/68*    (2006.01)

(52) U.S. Cl. .................. 702/19; 702/20; 435/6
(58) Field of Classification Search ............ None
See application file for complete search history.

(56) References Cited

U.S. PATENT DOCUMENTS 5,695,940 A    12/1997    Drmanac et al.
6,251,588 B1    6/2001    Shannon et al.

OTHER PUBLICATIONS

Rozen et al. (Methods in Molecular Biology, vol. 132, pp. 365-386).*
S. Patrick Walton et al., "Prediction of Antisense Oligonucleotide Binding Affinity and Activity in Cell Culture", Proceedings of The First Joint BMES/EMBS, Conference Serving Humanity, Advancing Technology, Oct. 1999 (abstract and p. 96).

* cited by examiner

*Primary Examiner*—Lori A Clow
(74) *Attorney, Agent, or Firm*—Venable LLP; Michael A. Gollin; Matthew E. Kelley

(57) ABSTRACT

A method for determining one or a set of optimal reagent oligonucleotide sequences used in a biochemical method for evaluating a target nucleic acid sequence having a target feature by defining a set of exclusion values or ranking values specific to the biochemical method, generating candidate reagent oligonucleotide sequences, evaluating the candidate reagent oligonucleotide sequences against the exclusion or ranking parameters, selecting at least one optimal reagent oligonucleotide sequence for the selected biochemical method as applied to the target nucleic acid sequence.

41 Claims, 42 Drawing Sheets

TGGTCATCGTGGCCATCGCC[C/T]GGACTCCGAGACTCCAGACC

FIG. 1A tggtcatcgtggccatcgccYggactccgagactccagacc

FIG. 1B tggtcatcgtggccatcgccCggactccgagactccagacc
tggtcatcgtggccatcgccTggactccgagactccagacc

FIG. 1C

21Ttggtcatcgtggccatcgcc Cggactccgagactccagacc

```
5'-tggtcatcgtggccatcgccCggactccgagactccagacc-3'
              tcgccCggactccga
              atcgccCggactccg
              catcgccCggactcc
              ccatcgccCggactc
              gccatcgccCggact
```

FIG. 4A

```
5'-tggtcatcgtggccatcgccTggactccgagactccagacc-3'
              tcgccTggactccga
              atcgccTggactccg
              catcgccTggactcc
              ccatcgccTggactc
              gccatcgccTggact
```

FIG. 4B

```
5'-ggtctggagtctcggagtccGggcgatggccacgatgacca-3'
                 agtccGggcgatggc
                 gagtccGggcgatgg
                 ggagtccGggcgatg
                 cggagtccGggcgat
                 tcggagtccGggcga
```

FIG. 4C

```
5'-ggtctggagtctcggagtccAggcgatggccacgatgacca-3'
                 agtccAggcgatggc
                 gagtccAggcgatgg
                 ggagtccAggcgatg
                 cggagtccAggcgat
                 tcggagtccAggcga
```

ProbeITy

File Edit View Insert Format Records Tools Window Help

Variations

Customer Name: Celadon          Gene: IGF1

| Name | Feature | Nuc-leotide | Amino Acid |
|---|---|---|---|
| IGF1_G214R | Exon | [G/A] | [G/R] |
| IGF1_K442E | Exon | [A/G] | [K/E] |
| IGF1_P325L | Exon | [T/C] | P325L |
| IGF1_T-1411C | Promoter | [T/C] | |

[Add New Variation]

[Cancel]  [< Back]  [Next >]  [Finish]

Form View

```
321 GTTATGTATA TCCAGTATCT GCCCCATGGT AG[A/G]TTCCTTT
361 TTTTGTGT TGGAGTTTTG CTCTTGTTGC CCAGGTTGGA
401 GTGCAATGGT GCAATCTTGG CTCACTGCAA CCTCAGCCTG
441 CTGGGTTCAA GCAATTCTCC TGCCTCAGCC TCCCGAGTAG
481 CTGGGATTAA GGCACGTGCC ACCACACCCG GCTAATTTTT
521 GTATTTTCAG TAGAGATGGG GGTTTCACCA TATTGGCCGG
561 GCTGGTCTCG AGCTCCTGAC CTCAGGTGAT CGGCCCATCT
601 CAGCCTCCCA AGTGCTGGGA TTACAGGTGT GAGCCACTGT
641 GCCTGGCCAG ATG
```

| | 5' | 3' | length |
|---|---|---|---|
| Upstream: | 1 | 352 | 352 |
| SNP: | 353 | 353 | 1 |
| Downstream: | 354 | 653 | 300 |

| | 5' | 3' | length |
|---|---|---|---|
| Left: | 236 | 342 | 107 |
| SNP: | 329 | 377 | 49 |
| Right: | 364 | 471 | 108 |

Sequence Stats:

Search Regions:

FIG. 7S

| Oligo Parameters | | | | |
|---|---|---|---|---|
| Parameter | Left Primer | Right Primer | Allele 1 Probe | Allele 2 Probe |
| Oligo Min Len | 18 | 18 | 15 | 15 |
| Oligo Max Len | 22 | 22 | 25 | 25 |
| Oligo Min Tm | 58 | 58 | 68 | 68 |
| Oligo Max Tm | 60 | 60 | 72 | 72 |
| Oligo Min GC | 20 | 20 | 20 | 20 |
| Oligo Max GC | 60 | 60 | 60 | 60 |
| Max Repeat Length | 3 | 3 | 3 | 3 |
| Allowed 5 End Bases | ACGT | ACGT | ACT | ACT |
| Allowed 3 End Bases | ACGT | ACGT | N/A | N/A |
| Max SW Self | 4 | 4 | 10 | 10 |
| GC Clamp Len | 3 | 3 | N/A | N/A |
| Oligo Conc | 300 | 300 | 300 | 300 |

Divalent Multiplier: 100
Max Pair Align Score: 8

FIG. 7V

SEQUENCE LISTING

```
<160> NUMBER OF SEQ ID NOS: 63

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tggtcatcgt ggccatcgcc yggactccga gactccagac c                           41

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gccatcgcct ggactccga                                                    19

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gccatcgcct ggact                                                        15

<210> SEQ ID NO 4
<211> LENGTH: 41
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 4
tggtcatcgt ggccatcgcc cggactccga gactccagac c                    41

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tggtcatcgt ggccatcgcc tggactccga gactccagac c                    41

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggtctggagt ctcggagtcc gggcgatggc cacgatgacc a                    41

<210> SEQ ID NO 7
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggtctggagt ctcggagtcc aggcgatggc cacgatgacc a                    41

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tgggcctgag ggccc                                                 15

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
agctgggcct gagggc                                                16

<210> SEQ ID NO 10
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 10
tgggcctgag ggcccc                                                      16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
ctgggcctga gggccc                                                      16

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
cgagctgggc ctgaggg                                                     17

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
agctgggccc gaggg                                                       15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
ctgggcccga gggcc                                                       15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tgggcccgag ggccc                                                       15

<210> SEQ ID NO 16
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 16
ccctcgggcc cagct                                                        15

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
ccctcgggcc cagctc                                                       16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
aggggccctc aggccc                                                       16

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
ccctcaggcc cagctcg                                                      17

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
ctgggcctga gggcc                                                        15

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
tgggcctgag ggccc                                                        15

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
```

```
      probe

<400> SEQUENCE: 22
agctgggcct gagggc                                                       16

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
ctgggcctga gggccc                                                       16

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
cgagctgggc ctgaggg                                                      17

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
agctgggccc gaggg                                                        15

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ctgggcccga gggcc                                                        15

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
ccctcgggcc cagct                                                        15

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 28
ccctcgggcc cagctc                                                    16

<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ccctcaggcc cagctc                                                    16

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
ccctcaggcc cagctcg                                                   17

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
ccctcgggcc cagct                                                     15

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
aggggccctc aggccc                                                    16

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 33
gtgcatagcc tctcct                                                    16

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 34
```
gtgcatagcc tctccta                                          17

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 35
ggaagtggag gtcgt                                            15

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 36
ttgggaagtg gaggtc                                           16

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 37
cttgggaagt ggaggt                                           16

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 38
accttgggaa gtggag                                           16

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 39
gaccttggga agtgga                                           16

<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 40
agaccttggg aagtgg                                           16

<210> SEQ ID NO 41
<211> LENGTH: 16
<212> TYPE: DNA
<213> ORGANISM: Artificial Sequence

```
<220> FEATURE:
<223> OTHER INFORMATION: Description of Artificial Sequence: Primer

<400> SEQUENCE: 41
ggagaccttg ggaagt                                                      16

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 42
tggagacctt gggaag                                                      16

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 43
ctggagacct tgggaa                                                      16

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 44
cctggagacc ttggg                                                       15

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 45
gcacctggag acctt                                                       15

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 46
ctccagcacc tggag                                                       15

<210> SEQ ID NO 47
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 47
tccagtttgc ctagca                                                      16
```

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 48
tctctccagt ttgccta                                                  17

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 49
gctctctcca gtttgc                                                   16

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 50
gagctctctc cagtttg                                                  17

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 51
tgagctctct ccagttt                                                  17

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 52
agtgaccctg ctgag                                                    15

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 53
cagtgaccct gctga                                                    15

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Primer

```
<400> SEQUENCE: 54
gacccagtga ccctg                                                   15

<210> SEQ ID NO 55
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 55
tgcagacaag aatgacc                                                 17

<210> SEQ ID NO 56
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 56
gtgcatagcc tctcct                                                  16

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 57
tccagtttgc ctagca                                                  16

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 58
ccctcgggcc cagct                                                   15

<210> SEQ ID NO 59
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 59
aggggccctc aggccc                                                  16

<210> SEQ ID NO 60
<211> LENGTH: 67
<212> TYPE: DNA
<213> ORGANISM: Artificial Sequence
<220> FEATURE:
<223> OTHER INFORMATION: Description of Artificial Sequence: Primer

<400> SEQUENCE: 60
gtgcatagcc tctcctatca gacgaggggc cctcgggccc agctcgcagg ttgctaggca    60
aactgga                                                            67
```

<210> SEQ ID NO 61
<211> LENGTH: 323
<212> TYPE: DNA
<213> ORGANISM: Unknown Organism
<220> FEATURE:
<223> OTHER INFORMATION: Description of Unknown Organism: Illustrative
      sequence

<400> SEQUENCE: 61

```
tccagtatct gccccatggt agrttccttt tttttgttgt tggagttttg ctcttgttgc      60
ccaggttgga gtgcaatggt gcaatcttgg ctcactgcaa cctcagcctg ctgggttcaa     120
gcaattctcc tgcctcagcc tcccgagtag ctgggattaa ggcacgtgcc accacacccg     180
gctaattttt gtattttcag tagagatggg ggtttcacca tattggccgg gctggtctcg     240
agctcctgac ctcaggtgat cggcccatct cagcctccca agtgctggga ttacaggtgt     300
gagccactgt gcctggccag atg                                             323
```

<210> SEQ ID NO 62
<211> LENGTH: 653
<212> TYPE: DNA
<213> ORGANISM: Unknown Organism
<220> FEATURE:
<223> OTHER INFORMATION: Description of Unknown Organism: Illustrative
      sequence

<400> SEQUENCE: 62

```
ctgcttctgt ggcatgtatc atgtctgaga aagaatggtg caccctgata ggtccacaca      60
gtgtcagaag gcaaggtggc caggtcacag gctgtcactt attaaaactg tgtcatagaa     120
agaccataca aatggaagtc agattctaat ttctattcag ttttcacctg gttgcatggc     180
cttgggcatg tcattttgtc tccccagacc tcagttttct catctgcaaa aggttagggg     240
tcttctatta gctgagagga ctattaggag aattaaaagt gagcttcctc taggcagaaa     300
tcatgtctgt tcacgtagaa gttatgtata tccagtatct gccccatggt agrttccttt     360
tttttgttgt tggagttttg ctcttgttgc ccaggttgga gtgcaatggt gcaatcttgg     420
ctcactgcaa cctcagcctg ctgggttcaa gcaattctcc tgcctcagcc tcccgagtag     480
ctgggattaa ggcacgtgcc accacacccg gctaattttt gtattttcag tagagatggg     540
ggtttcacca tattggccgg gctggtctcg agctcctgac ctcaggtgat cggcccatct     600
cagcctccca agtgctggga ttacaggtgt gagccactgt gcctggccag atg             653
```

<210> SEQ ID NO 63
<211> LENGTH: 333
<212> TYPE: DNA
<213> ORGANISM: Unknown Organism
<220> FEATURE:
<223> OTHER INFORMATION: Description of Unknown Organism: Illustrative
      sequence

<400> SEQUENCE: 63

```
gttatgtata tccagtatct gccccatggt agrttccttt tttttgttgt tggagttttg      60
ctcttgttgc ccaggttgga gtgcaatggt gcaatcttgg ctcactgcaa cctcagcctg     120
ctgggttcaa gcaattctcc tgcctcagcc tcccgagtag ctgggattaa ggcacgtgcc     180
accacacccg gctaattttt gtattttcag tagagatggg ggtttcacca tattggccgg     240
gctggtctcg agctcctgac ctcaggtgat cggcccatct cagcctccca agtgctggga     300
ttacaggtgt gagccactgt gcctggccag atg                                   333
```

COMPUTER SYSTEM FOR DESIGNING OLIGONUCLEOTIDES USED IN BIOCHEMICAL METHODS

This application claims the benefit under 35 USC Section 119(e) of U.S. provisional application 60/237,383, filed Oct. 4, 2000.

BACKGROUND OF THE INVENTION

The invention is in the field of bioinformatics and provides methods and systems for generating optimal reagent oligonucleotides for use in biochemical methods, for comparing and evaluating biological sequences, for providing sequences of biological molecules in a relational format allowing retrieval in a client-server environment, and for creating libraries of DNA hybridization probes.

The invention provides and methods for comparing and evaluating biological sequences, for providing sequences of biological molecules in a relational format allowing retrieval in a client-server environment, and libraries of DNA hybridization probes.

All populations of organisms exhibit genetic diversity. In any particular population, the extent, kind and structure of genetic diversity is influenced by the biological processes of mutation and recombination, as well as the population genetic processes of natural selection and random genetic drift. The effect of these processes depends on population size, subdivision and history, as well as mating patterns. A newly arisen variant may confer an evolutionary advantage or disadvantage, or it may be neutral. Natural selection may remove a disadvantageous variant from a population, drive a favored variation to fixation, or maintain polymorphism due to balancing effects. Loss, fixation or polymorphism of neutral variations may occur due to chance events. (Hartl, D., and Clark, A., *Principles of Population Genetics*, $2^{nd}$ Ed., Sinauer Assocs, Inc., Sunderland, Mass. © 1989).

Hybridization methods to score genetic diversity have not realized their potential. A primary cause for this is that software has been unavailable to comprehensively analyze the nucleic acid sequence context of a targeted variation. Because of this, there are differential success rates across laboratories. Laboratories that happen to have researchers who are either lucky or who develop a touch for a method are able to achieve allelic discrimination in some 70 to 90 out of 100 designed assays based on "brute force" approaches alone. Other labs, with less experienced or less lucky researchers, often have little or no success, failing to get even a single assay to perform well. Assessing millions of genetic polymorphisms in tens, hundreds, and thousands of biological samples represents an enormous task.

In order to more efficiently score genetic polymorphism, a number of molecular biology methods have been developed. One method is "single base extension", a form of nucleotide sequencing. In this method, an oligonucleotide sequencing primer is extended by just one base, and this base is complementary to the targeted variation.

Additional methods include hybridization methods such as oligonucleotide arrays, for example PCT Application WO 99/05324, molecular beacons, Invader, the 5' nuclease method, and DASH (Howell et al., (1999) *Nat. Biotech.* 17:87-88). The principle underlying these methods is that an oligonucleotide will bind more strongly to a target DNA sequence when there is perfect, complementary Watson-Crick base pairing compared to when there is one or more mismatches between the oligonucleotide probe and the complementary target sequence. Ideally, probe hybridization should be digital. That is, a probe should always hybridize to its perfectly complementary sequence and never hybridize to sequence that is not perfectly complementary.

Despite the recent completion of drafts of the human genome and other genomes, and the identification of millions of genetic polymorphisms, to date only a tiny fraction of genetic diversity has been studied with respect to medically and commercially important traits. The small number of studied polymorphisms is largely due to the large amount of work required of conventional laboratory methods and processes. One aspect of conventional methods that is particularly labor intensive is the design of assays, and most particularly the design of oligonucleotide primers or probes used therein. Present design methods often results in sub-optimal assays that require extensive laboratory optimization in order to obtain meaningful signals while keeping nonspecific biological background interference, primer dimerazation, and oligonucleotide secondary structure formation to a minimum (Saiki, et al. (1985) *Science* 37:170-172). This is especially true for methods that use hybridization probes to discriminate among genetic variations.

It would be highly useful to apply SNP scoring and especially hybridization methods to the study of genetic diversity on a large scale. For example, it would be useful to study the association between certain variations and susceptibility or resistance to specific diseases, or to drug response. To accomplish these benefits will require the large-scale design of oligonucleotides to be used as PCR primers, allele-specific hybridization probes, and to perform other functions. Further, it will require storing a vast amount of data in such a way as to ease later querying and retrieval. What is needed is an improved process and methods suitable for large-scale design of genetic diversity assays and systems and methods for organizing large amounts of data used in genetic diversity studies.

The first previous approach is PrimerExpress™ Software from Applied Biosystems. This software functions as a calculator where the user must input each sequence individually. Thus, comprehensive examinations are not performed. This software does not allow specification of the targeted genetic variation, does not automatically examine both the forward and reverse strands of the DNA molecule, does not automatically evaluate primer and probe sequences for more than one model, and does not communicate with a central database. Better software would be process oriented, such that it leads the user through the design process, requiring little user interference. Such software would also operate in batch mode, being able to process a queue of variations.

The second previous approach is MeltCalc software. This is implemented in an Excel spreadsheet. This software functions as a calculator, but also examines some of the surrounding sequence. It appears that this software (PrimeExpress™) does not perform a comprehensive examination, does not automatically examine both the sense and antisense strands of the DNA molecule, does not evaluate primers in addition to probes, is specific to one model, does not communicate with a central database and is not process oriented.

Many molecular biology methods for scoring genetic variation require the use of one or more reagent oligonucleotides. Each of these reagent oligonucleotides performs a separate function and these functions are well known in the art. These functions include, but are not limited to, forward PCR primer, reverse PCR primer, sequencing primer, allele-specific hybridization probe, anchor probe, invader probe, and reporter-probe. Typically, many candidate oligonucleotides can be considered for each function. The problem is to choose typically one oligonucleotide for each function such that the oligonucleotides for all functions perform well in combination to produce excellent allelic discrimination. In addition it is important to design reagent oligonucleotides that are not cross reactive or inhibitory, for example, to minimize primer dimerization or reagent oligonucleotide cross complementarity, so that the biochemical method employed to evaluate target nucleic acid sequences is most efficient.

Prior approaches resulted in sub-optimal assays because only a few of the candidate reagent oligonucleotides were examined one at a time by researchers. This is slow, laborious and resulted in many failed assays and much laboratory time and cost to optimize reaction conditions.

SUMMARY OF THE INVENTION

The invention provides computer software products to be used by scientists. Compared to existing software, the provided computerized method more quickly designs better reagent oligonucleotides for performing biochemical methods.

The invention automatically performs a comprehensive examination of nucleotide sequences adjacent to target features within target nucleic acid sequences such that all candidate reagent oligonucleotide sequences (e.g., primers and probes) are available for evaluation by one or more defined biochemical methods. The sequence to be examined optionally originates from a database, and the assay design selected by the model or chosen by the user is optionally committed to a database. The comprehensive examination algorithm is distinct from the model that is applied to evaluate potential primers and probes.

According to one aspect of the invention, a computer system is used to methodically and comprehensively examine the nucleotide sequence flanking a targeted polymorphism. This examination is comprehensive in that, for a given method, all candidate reagent oligonucleotides that can be used in the method to query the targeted feature (e.g. single nucleotide polymorphism) are considered. One or more biochemical models (e.g., Polymerase Chain Reaction, Reverse Transcriptase-Polymerase Chain, ReactionNucleotide™ Sequencing, Fluorescent in situ hybridization, allele-specific oligonucleotide hybridization (ASOH), dynamic allele-specific hybridization (DASH), antisense oligonucleotide chemistry, nucleic acid hybrid chemistry, DNA/RNA repair, etc.) can be applied to a targeted feature. Each model may have a unique set of possible oligonucleotides. For a given model, each possible oligonucleotide is evaluated with respect to the variables, parameters, and constraints of the model. An oligonucleotide is retained for further analysis only if it satisfies the exclusion constraints of the model. The resulting list of oligonucleotides may have zero or more entries. These entries are sorted based on one or more ranking parameters of the model.

The steps involved are: inputting nucleotide sequence which contains a targeted polymorphism; examining one strand (sense or antisense) for one allele of the polymorphism so as to determine an oligonucleotide that perfectly matches the complement of the allele; comparing this oligonucleotide to the complement of alternate alleles in order to assess the ability of the oligonucleotide to provide predicted allelic discrimination; saving the oligonucleotide for further analysis only if it satisfies the constraints of the model; repeating until all possible oligonucleotides have been considered; optionally repeating for all alleles; optionally repeating for the opposite strand; optionally repeating for all specified models; sorting the resulting lists based on one or more model variables; optionally presenting the lists to the user for further evaluation and selection; optionally choosing the oligonucleotides that best satisfy predetermined model constraints; optionally repeating until all targeted polymorphisms have been processed.

In sum, the invention provides a method for determining an optimal reagent oligonucleotide sequence for use in a biochemical method for evaluating a target nucleic acid sequence having a target feature, the method comprising the steps of defining a set of exclusion values and/or ranking values specific to the biochemical method, defining a sequence window adjacent to the target feature, generating candidate reagent oligonucleotide sequences complementary to one or both of the sense and antisense strands of the target nucleic acid sequence within the sequence window, the reagent oligonucleotide sequences having a length less than or equal to the sequence window, evaluating the candidate reagent oligonucleotide sequences against the exclusion and/or ranking parameters, selecting at least one optimal reagent oligonucleotide sequence for the selected biochemical method as applied to the target nucleic acid sequence.

The invention also provides a computer readable data storage medium storing a computer readable program code means for causing a computer to perform the steps of the provided method and a computer system comprising the data storage medium.

Additionally, the invention provides a process of manufacturing reagent oligonucleotides comprising using reagent oligonucleotide sequences from the provided computer system in a nucleic acid synthesizer to produce the selected reagent oligonucleotides.

Further, the invention provides a kit of a predetermined number of reagent oligonucleotides optimized for a biochemical method used in evaluating a target nucleic acid sequence, the reagent oligonucleotides made by the provided process.

Lastly, the invention provides a method of ordering a kit of reagent oligonucleotides by accessing the provided computer system, inputting the desired target nucleic acid sequence, generating a set of reagent oligonucleotide sequences useful in one or more biochemical methods used in evaluating said target nucleic acid sequence, selecting and ordering the desired sequences from the list of generated reagent oligonucleotide sequences, synthesizing a kit of reagent oligonucleotides based on the selected reagent oligonucleotide sequences, and shipping said kit of reagent oligonucleotides.

BRIEF DESCRIPTION OF THE DRAWINGS

FIG. 1 shows several recognized nucleic acid sequence formats. Upper and lower case used for emphasis only. Brackets ([ ]) and slash (/) can be any delineating characters. Sequences shown in the 5' to 3' direction. "A" (SEQ ID NO: 1) shows sequence in WhiteHead-Affymetrix format, "B" (SEQ ID NO: 1) shows sequence in IUPAC format, "C" (SEQ ID NO: 1) shows sequence in allelic format, and "D" (SEQ ID NO: 1) shows sequence as it appears in a database (e.g., BLAST or FASTA formats) where the number is the position in specified sequence and the letter designation is a variant allele.

FIG. 2 shows the numbering systems used to indicate the relative positions of nucleotide bases used in the present invention. "A" (SEQ ID NO: 2) shows a portion of a sequence window region for an allele-specific hybridization probe where the position of the polymorphism is designated "0" and the nucleotides 5' or upstream to the polymorphism are descending negative and 3' or downstream are ascending positive. "B" (SEQ ID NO: 3) shows an oligonucleotide designed by the present invention that could be used as an oligonucleotide-probe, or primer; the numbering scheme herein designates the first nucleotide of the oligonucleotide as "1" and 5' or upstream nucleotides are number in ascending numerical order.

FIG. 4 shows an example of the complementary candidate oligonucleotide generated using the present invention in a sequence window. The illustrative target nucleic acid sequence of 15 base pairs contains polymorphic base in the middle third of the oligonucleotide. "A" (SEQ ID NO: 4 and residues 16-30, 15-29, 14-28, 13-27 and 12-26 of SEQ ID NO: 4) shows a sense strand of the target nucleic acid and the candidate reagent oligonucleotide that is complementary thereto at polymorphic base C; "B" (SEQ ID NO: 5 and residues 16-30, 15-29, 14-28, 13-27 and 12-26 of SEQ ID NO: 5) shows a sense strand of the allele with polymorphic base T; "C" (SEQ ID NO: 6 and residues 16-30, 15-29, 14-28, 13-27 and 12-26 of SEQ ID NO: 6) shows an antisense strand of the allele with polymorphic base G; and "D" (SEQ ID NO: 7 and residues 16-30, 15-29, 14-28, 13-27 and 12-26 of SEQ ID NO: 7) shows an antisense strand of the allele with polymorphic base A.

FIGS. 5A-O are screen shots of the graphical user interface screens (desktop version) provided for accepting user queries, inputs of nucleic acid sequence and for the display of results generated using the present invention.

FIG. 5A shows the screen shot depicting a scatter plot of results obtained from the invention for adenine→guanine purine to purine point mutation in the drd2 encoding nucleic acid sequence. The abscissa measures the fluorescence emitted by a hybridization probe to the allele with an A polymorphism, and the ordinate measures the fluorescence emitted by a hybridization probe to the allele with an G polymorphism, each dot represents a sampled organism.

FIG. 5B shows a plurality of genetic sequences available in the database for a project and the highlighted selection of the IGF1 encoding nucleic acid sequence.

FIG. 5C shows the genetic variations entered into the database for the IGF1 gene and the selection of the IGF1_P325L allele, wherein the polymorphism changes amino acid 325 of the encoded protein. The targeted polymorphism and flanking sequence are examined with respect to the correct sequence format.

FIG. 5N shows a screen wherein the assay is given an arbitrary name, the genetic locus or nucleic acid sequence under examination, the name of the method used and variable fields that identify the submitter of the assay.

FIG. 5O shows the selection screen for a Sequence Tagged Site name and the name for both forward and reverse oligonucleotide primers.

FIG. 6A shows a nucleotide fragment with the location of Examination Regions for the 5' nuclease method (TaqMan™, Applied Biosystems, Inc.). "A" shows the site at which the forward PCR primer anneals, "B" shows the site at which the allele specific probe(s) anneal(s), "C" shows the site at which the reverse PCR primer anneals, "X" indicates the targeted feature.

FIG. 6B shows a nucleotide fragment wherein the location of Examination Regions for 5' nuclease method with minor groove binding (MGB) probes (TaqMan, Applied Biosystems). "A" shows the site at which the forward PCR primer anneals, "B" shows the site at which the allele specific probes anneal with conjugated a minor groove binder group (601), "C" shows the site at which the reverse PCR primer anneals, "X" indicates targeted feature.

FIG. 6C shows a nucleotide fragment with the location of Examination Regions for the anchor method (Light Cycler, Roche). "A" shows the site at which the forward PCR primer anneals, "B" shows the site at which the allele-specific probe(s) anneal, "C" shows the site at which the anchor probe anneals, and "D" shows the site at which the reverse PCR primer anneals. "X" indicates the targeted feature.

FIG. 6D shows a nucleotide fragment with the location of Examination Regions for the Invader method (Third Wave). "A" shows the site at which the allele-specific Invader Probe anneals, "B" shows the site at which the signal probe with line indicating displacement of 5' end anneals. "X" indicates the targeted feature.

FIG. 6E shows a nucleotide fragment with the location of Examination Regions for the single base extension method (Orchid Bioscience, Inc.) "A" shows the site at which the forward PCR primer anneals, "B" shows the site at which the sequencing primer anneals, "C" shows the site at which the reverse PCR primer anneals. "X" indicates the targeted feature.

FIG. 6F shows a nucleotide fragment with the location of Examination Regions for the DASH method. "A" shows the site at which the forward PCR primer anneals, "B" shows the site at which the allele specific probe(s) anneal, "C" shows the site at which the reverse PCR primer anneals. "X" indicates the targeted feature.

FIGS. 7P-7V (SEQ ID NO: 61 found in FIG. 7Q, SEQ ID NO: 62 found in FIG. 7R and SEQ ID NO: 63 found in FIG. 7S) are web-based client screen shots for a system analogues to the desktop version of the software package as in the present invention as depicted in FIGS. 5A-5O.

DETAILED DESCRIPTION

Figure 3:
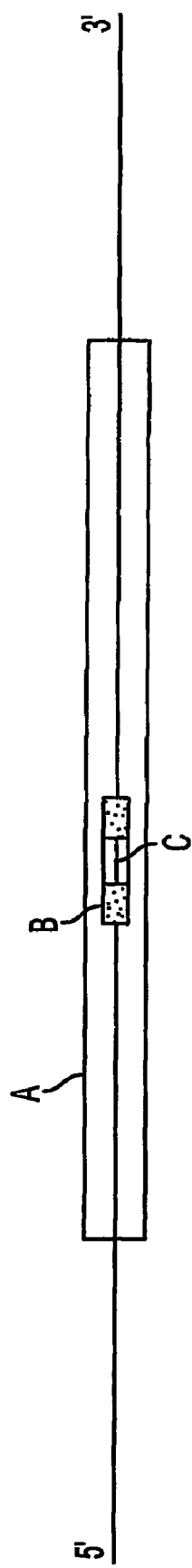
FIG. 3 is a depiction of a nucleotide sequence under examination having an Examination Region, "A", Sequence Window, "B" and Open Positions "C".

In describing preferred embodiments of the present invention illustrated in the drawings, specific terminology is employed for the sake of clarity. However, the invention is limited to the specific terminology so selected. It is to be understood that each specific element includes all technical equivalents which operate in a similar manner to accomplish a similar purpose. Each reference cited here is incorporated by reference in its entirety as if each were individually incorporated by reference.

Disclosed is an improved computer-aided process and method for generating and evaluating oligonucleotides used in a variety of customized or commercially available molecular biology methods. The present invention is primarily illustrated, but is not limited to, the design of optimized oligonucleotide primer pairs for the 5' nuclease method (TaqMan™, Applied Biosystems, Inc); this results in allelic discrimination with a success rate above 90%.

The invention also provides a relational database system for storing, organizing, and displaying target nucleic acid and reagent oligonucleotide sequence information together with sequence annotations; such as allele variation detail, the information important to evaluating, studying, and cataloging the genetic diversity of a species.

The term "adjacent" as used herein describes the distance of the sequence window from the target feature (in either the 3' or 5' directions) ranging in practice from overlapping or encompassing to a distance of 30 kb away from the target feature, the distance being the limits of the amplification technology to "reach" the target feature from that distance. For sequence windows that do not overlap the target feature these sequence windows are primarily used for selecting reagent oligonucleotide sequences that act as amplification primers. It is known in the art that long range PCR amplification methods can generate amplicons that are more than about 40 kb in length (Barnes et al. (1994) Proc. Natl. Acad. Sci. USA 91: 221 & 2220, see also www.genecraft.de-/products/48.htm).

The term "biochemical method" or "biochemical model," and the like, as used herein shall include any chemical and biochemical protocols, methods, models, reactions, experiments, diagnostic, techniques, and assays for evaluating target nucleic acid sequences. The term "evaluating" as used herein includes all methods of nucleotide processing such as amplification, reverse transcription, transcription, translation, immobilization, cloning, hybridization, sequencing, antisense biochemistry, RFLP, DNA or RNA repair, mutagenesis biochemistry, site-specific mutagenesis, and mutagenic recombination.

The terms "optimal," "optimized" and the like as used herein describes the best fit of a reagent oligonucleotide sequence within the exclusion and ranking parameters of a selected biochemical method. An "optimal set" or "solution set" of reagent oligonucleotides also satisfies compatibility criteria.

An "evaluating parameter" refers to physical or chemical properties of the candidate reagent oligonucleotide sequences necessary for the sequences to perform well in a given biochemical method. Examples include thermodynamic parameters, amplicon parameters, oligo parameters, secondary structure parameters, and sequence parameters, all of which are explained in greater detail below. For each evaluating parameter, there are exclusion, ranking, and/or compatability values, which are predetermined constraint values for a particular parameter. Exclusion values (typically a minimum and a maximum or presence and absence) are used to test candidate sequences, in a pass/fail mode. For ranking values, the constraints provide an ideal value or range of values against which candidate sequences are evaluated. For compatibility values, the constraints ensure that candidate reagent oligonucleotides of a candidate set are compatible, e.g. not self inhibitory, cross reactive, or cross complementary with each other (e.g., formation of secondary structures with each other, primer dimerization, competitive inhibition, accidental ligation, circularization, or inherent catalytic activity such as ribozymes or lariats).

The term "reagent oligonucleotide sequences" as used herein generally refers to the sequence information (e.g., order of adenines, guanines, cytosines, and thymidine) for a oligonucleotide used in as a reagent in a Biochemical method. This information can be in written form, computer readable form; such as but not limited to text, ASCII, RTF, MSWord, or any other computerized text format, or can be in a computer readable form that has been encrypted, formatted in HTML, or in any other coded form. The term "reagent oligonucleotides" is generally used here to mean the physical oligonucleotide which has been synthesized using any oligonucleotide synthesis technique known in the art which is used as a reagent in a biochemical method. A person of ordinary skill will understand that reference to a sequence connotes the oligonucleotide, and vice versa The term "sequence window" means a section of either or both of the sense or antisense sequence of the target nucleic acid sequence selected for generating potential candidate reagent oligonucleotide sequences that are complementary to the target nucleic acid sequence (in particular to evaluate the target feature). The sequence window has a length of nucleotide bases/base pairs that is less than or equal to the length of the entire target nucleic acid sequence, and is greater than or equal to the minimum useful length of a candidate oligonucleotide. In the typical embodiment where the sequence window length is less than the entire target nucleic acid, all possible candidate reagent oligonucleotides complementary to the target nucleic acid within the sequence window are considered. The possible candidate oligonucleotides to be considered are generally constrained by the exclusion values for the size parameter. For example, if the maximum length of a reagent oligonucleotide sequence (e.g., for a primer or probe), as constrained by the length parameter, is 35 bp then the sequence window is 35 bp. If the length parameter constraint minimum is 10 bp, then all possible reagent oligonucleotide sequences of lengths 10-35 within the sequence window will be considered. The location of the sequence window and adjacency to the target feature in the target nucleic acid sequence, is dependent on the particular biochemical method used and type of reagent oligonucleotide required. According to the invention, the sequence window can be repositioned along the target nucleic acid sequence according to the constraints of the biochemical method. For example, if the biochemical method employed is PCR and the reagent oligonucleotide sequences evaluated are forward and reverse primers; the PCR method able only to generate amplicons having a maximum length of 100 bp and use primers of maximum length 30 bp, then a 30 bp sequence window will be created and repositioned along the desired amplicon containing the target feature until all candidate reagent oligonucleotides sequences useful in making such an amplicon are generated for consideration. The sum of the range of positions within which the sequence window may be stepped (or incremented or repositioned) can be referred to as the "examination region," which in this case would be 100 bp (see FIG. 3). For a probe, the sequence window and the examination region would typically be coextensive (the same).

The term "target nucleic acid sequence" means a double or single stranded DNA or RNA, chimera/hybrid, or analogue comprising a sequence of adenines, guanines, cytosines, thymidines, or uracils, under evaluation. The target nucleic acid sequence has one or more target features. "Target feature" means a sub-sequence of a target nucleic acid sequence of interest to the researcher, such as a single nucleotide polymorphism, a multimeric subsequence of the target nucleic acid sequence, a cloning sequence, the entire target nucleic acid sequence under examination, a codon, an exon, an intron, a telomere, a viral sequence, a transposon, a noncoding region, a promoter, an enhancer sequence, an expressed sequence tag, and a sequence tagged site.

Oligonucleotide Design

A key aspect of the invention is the process of methodically performing a comprehensive examination and evaluation of the nucleotide sequence flanking a polymorphism so as to arrive at a combination or set of oligonucleotides per biochemical method or model. This set is optimal in that it maximizes the predicted chance of yielding the highest allelic discrimination. The present invention identifies all oligonucleotides that satisfy the constraints of a specified biochemical model.

Figure 9:
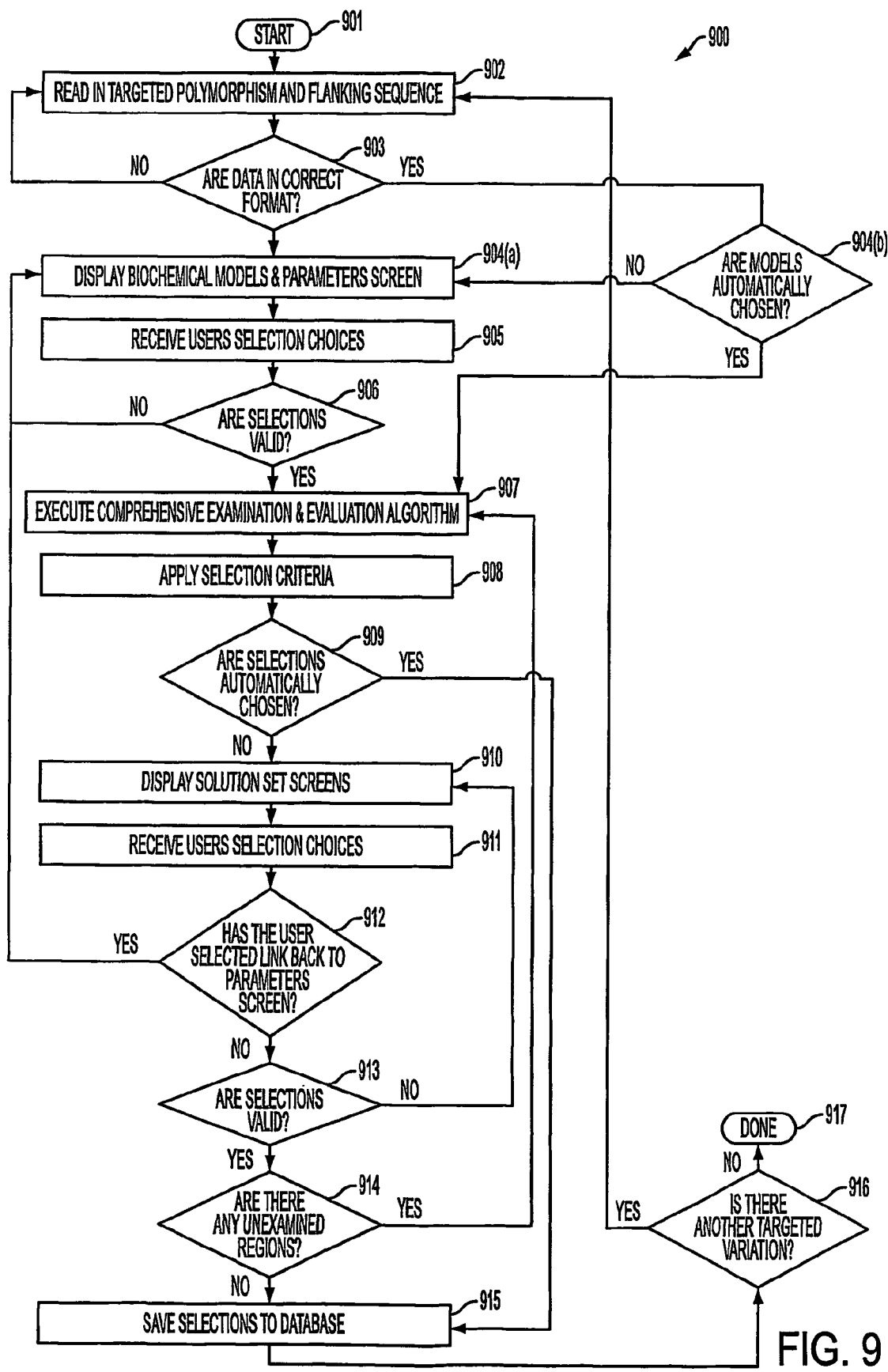
FIG. 9 is a flow chart showing an overview of the process of the present invention.

An overview of the process in FIG. 9 (900), for each reagent oligonucleotide sequence, to generate all possible candidate reagent oligonucleotide sequences that have a length between some non-constraining minimum and some non-constraining maximum number of nucleotide positions. Each of these candidate oligonucleotides is evaluated with respect to some biochemical model parameterized according to the molecular biology method and oligonucleotide function under consideration. The candidates that satisfy the constraints of the model are retained and sorted based on one or more variables of the model. The zero or more candidates that maximize the predicted chance of producing excellent allelic discrimination are at, or near, the top of the sorted list.

First an allele of a nucleic acid sequence having at least one polymorphic site is entered via a graphical user interface (901) and read (902). Optionally, the data comprising the entered nucleotide sequence can be saved in a memory buffer for later access and to facilitate the creation of a data entry in a relational database. The software then checks whether the entered nucleic acid sequence conforms to known sequence file formats (903) which include but are not limited to, FASTA, MSF, NBRF, NEXUS, PHYLIP, raw ASCII, text, WhiteHead-Affymetrix format, or IUPAC formats (Baxevanis et al., eds., *Bioinformatics: A Practical Guide to the Analysis of Genes and Proteins*, Wiley-Interscience, New York, © 1998, pgs. 359-362 (Appendix 2)). The software is customizable to default to one biochemical method or can be modified to include a plurality of user selectable (905, 906) biochemical methods that employ oligonucleotides (904a, 904b). Upon entry of the allelic nucleic acid sequence under study, the software runs the algorithm (907) based on the selection parameters required by the respective biochemical method and determines a set of putative oligonucleotides that can be used in the respective biochemical method to study the allelic nucleic acid sequence. Concurrently, the software of the underlying method of the present invention performs an optimization subroutine which selects (908) among the several determined oligonucleotide sequences for the optimum for that biochemical method. The selected oligonucleotides are the candidate set and are displayed in descending optimal value (910). The scientist/user then selects which oligonucleotides she wishes to employ (911) and can then restart the process for a oligonucleotide selection in another biochemical method (912) and for any additional polymorphic regions of the entered allelic nucleic acid sequence that may require another run of the software (913, 914). After all of the oligonucleotides corresponding to the entered nucleic acid sequence and desired biochemical method(s) have been determined and selected, the user may optionally save the information into a relational database (915) that serves to catalogue the genetic variation of the entered nucleic acid sequence (916) and the determined oligonucleotides useful in its study. The user may opt to enter another allelic sequence, another polymorphism for an existing sequence, or terminate the program (917).

Algorithm and Comprehensive Examination

The invention defines discrete steps of the oligonucleotide assay design process and leads users through each step in a wizard-like fashion. The invention includes means for inputting target sequences into the software, validating target sequences to ensure proper formatting, displaying and describing the entered target nucleic acid sequence for user verification and comfort, defining a sequence window for each functional reagent oligonucleotide sequence in the biochemical method from which candidate reagent oligonucleotide sequences are generated, enabling a user to choose a predefined set of parameter values, enabling the user to customize parameter values for a specific design run instance, automated generation, constraint evaluation and scoring of candidate reagent oligonucleotide sequences for each window in a method-specific manner, displaying and enabling a computer graphical user interface ability to select one or more candidate oligonucleotides; or sets of candidate reagent oligonucleotides for consideration at subsequent steps of the design process, enabling the navigation back and forth through the design process so as to modify previous actions, enabling the selection of one or more biochemical methods, or individual oligonucleotides of an assay, enabling the fully automated design process by having the system select entire assays rather than individual candidate oligonucleotides, enabling the processing of more than one sequence either by stepping through the design process for each sequence consecutively or to automatically generate assays for each sequence in batch mode.

Further, the assay design process is integrated into an E-commerce platform that includes, user name and password protection for system entry and security, user registration with contact information, marketing survey at time of registration, user accounts that record personal contact, billing and shipping information and that track order history, shopping cart features that allow users to purchase one or more assays per sequence. The system is also designed to feed directly into a manufacturing operation. Specifically, the purchased oligos and relevant manufacturing instructions can be electronically downloaded automatically or manually and imported into the instruments that synthesize the actual oligonucleotides.

One novel aspect of the invention is the definition of a separate sequence window for each reagent oligonucleotide of an assay. Once each sequence window is chosen, the process of generating, evaluating and scoring candidate oligonucleotides is the same.

The generation of the list of candidate reagent oligonucleotides is methodical. The steps are:

Start at the first sequence position of the window the first candidate oligonucleotide starts at that position and has length determined by the parameter MinOligoLength or the end of the window, whichever is shorter.

Continue to generate oligonucleotides that start at this sequence position by incrementing the length by one until attainment of either the MaxOligoLength or the end of the window.

Move to the next sequence position and repeat the process until the start sequence position is less than MinOligoLength positions from the end of the sequence window.

The evaluation of the min and max constraints is also methodical. For each parameter, the corresponding property is calculated for each candidate reagent oligonucleotide sequence. Each property is evaluated with respect to the min and max values. If the property is greater than or equal to the min and less than or equal to the max, the candidate reagent oligonucleotide sequence satisfies the constraints and is marked as pass. Otherwise, the candidate reagent oligonucleotide sequence fails and is marked as fail.

Oligonucleotides that pass the constraints are then scored according to the ranking parameter. For each parameter, this function measures the distance of the oligonucleotide property from the ideal value and then multiplies this distance by the Weight parameter. Scores for each parameter are then summed to arrive at a single, composite score. Distance is measured by the absolute value of the difference between the ideal value and the property value. However, other distance measures are equally viable, such as the squared difference or the unit variance of the property based on a statistical or empirical distribution. Min and max constraints can be applied to this score. Typically, candidate oligonucleotides are displayed to the user sorted by score.

Alternatively, candidate oligonucleotides are not evaluated for the min and max constraints, but are simply scored and sorted on this score. Another option is to score candidate oligonucleotides and then to apply the min and max constraints. One set of min and max constraints could be applied to the score property.

The parameters used in the present invention are described below. Each of these parameters typically has four sub-parameters: Min, Ideal, Max and Weight. The Min and Max values are constraints that a candidate oligonucleotide must satisfy; to be considered in an assay, a reagent oligonucleotide sequence's property must be greater than or equal to the min and less than or equal to the max. The Ideal parameter is the value most desired by the user; this value is used in the scoring function that ranks candidate oligonucleotides that satisfy the min and max constraints. The Weight parameter is used in the scoring function and allows a user to adjust the relative importance of each parameter.

Exemplary evaluating parameters and constraint values used in the invention include some or all of the following, depending on the biochemical model and other factors. A person having ordinary skill in the art will readily be able to select from these parameters and values and others.

Thermodynamic Parameters

OligoTm

The temperature at which half of the oligos are in the single stranded state and half are in the double stranded state. Melting temperature is critical to oligonucleotide performance because genomic applications are tuned to specific Tms. The $T_m$ of PCR primers is typically 58-60 degrees. Other genomic applications, such as TaqMan, require hybridization probes that have a target $T_m$ of 68-70 degrees.

Typically $$T_m = \frac{dH}{\left(dS + R\ln\left(\frac{C}{4}\right)\right)} - 273.15,$$

wherein H is enthalpy, S is entropy, R is the gas constant (1.987 cal/mol·K), and C is concentration in units Molar.

BufferMg++

The concentration of Mg++ divalent ions in the buffer. Mg++ is a necessary cofactor for DNA-directed DNA polymerases. Higher concentrations increase $T_m$. Most biochemical methods utilize values ranging from 2.0 mM to 5.0 mM.

BufferK+

The concentration of salts such as K+ and Na+ help enhance hybridization by neutralizing the negative charge of the backbone. Higher salt concentrations increase $T_m$. Typical values range from 40 mM to 60 mM.

DivalentMultiplier

The relative affect on $T_m$ of divalent ions, such as Mg++, as compared to monovalent ions such as K+, is a matter of empirical uncertainty. Some researchers report a 100-fold difference, while others report a 150 fold difference. The DivalentMultiplier parameter allows this difference to be adjusted by the user.

Oligonucleotide Concentration

Increasing the concentration of an oligonucleotide increases its $T_m$. Typical values range from 0.1 µM to 1.0 µM.

AmpliconTm

An amplicon is the sequence amplified by a left and a right PCR primer. The melting temperature of an amplicon should be high enough so as to not interfere with oligonucleotide hybridization (55-70) or polymerase extension (70-75), and low enough that the two strands of the amplicon are fully disassociated at the melting temperature (94-96).

Amplicon Parameters

Amplicon Length
1. The number of base pairs in the amplicon, including the left and right PCR primers. PCR is typically most efficient for short amplicons. Typical limits are 10 to 150 base. Other applications, such as sequencing, SSCP or dHPLC, target amplicons within a certain range, such as 150 to 300 bp.

AmpliconGC
The number of Gs plus the number of Cs in the amplicon divided by the total number of base pairs in the amplicon. Typically, 50% GC/AT content is desired. Uneven GC content can result in poorly understood thermodynamics. It can also reduce the polymerases' ability to synthesize a new strand by causing slippage or by the presence of secondary structures that inhibit the polymerases' ability to traverse the strand.

Oligonucleotide Parameters

OligoLength
The number of base pairs in the oligonucleotide. In the present invention, OligoLengthMin and OligoLengthMax are the key parameters used to methodically generate all possible candidate oligos for a sequence. The typical range is between 10 and 40 base pairs. In the absence of accurate $T_m$ prediction, early PCR rules suggested oligos of about 20 base pairs and about 50% GC content. In some applications, such as allelic discrimination, shorter hybridization oligos are preferred because they more easily discriminate single base allelic differences.

OligoGC
The number of Gs plus the number of Cs in the oligonucleotide divided by the total number of nucleotides in the oligonucleotide. Typically, 10% to about 90%, with 50% GC/AT content preferred. Uneven GC content can result in poorly understood thermodynamics. It can also reduce the polymerases' ability to synthesize a new strand by causing slippage or by the presence of secondary structures that inhibit the polymerases' ability to attach to the double strand formed by the oligonucleotide and its template.

OligoMonoNucRunLength
The longest contiguous stretch of identical nucleotides. Runs of a single nucleotide can cause polymerase slippage or secondary structures that inhibit the ability of the polymerase to attach to the double strand formed by the oligonucleotide and its template.

Oligo5EndLinker
The chemical entity used to link a molecule to the end of an oligonucleotide. This information may be descriptive and used only in the manufacture of the oligonucleotide. In other situations, the effect of the linker is taken into account when predicting $T_m$.

Olio5EndModification
The molecule that is linked to the 5' end of the oligonucleotide. There are a large number of modifications of which the most frequent are fluorescent dyes. This information may be purely description and used only in the manufacture of the oligonucleotide. In other situations, the effect of the linker is taken into account when predicting $T_m$.

Oligo5EndTail
DNA sequence added to the 5' end of an oligonucleotide. This is sometimes used to allow for a second round of PCR using a standard PCR primer; to create secondary structure, such as for molecular beacons; or to increase the length of the primer, such as for single base extension.

Oligo5EndAllowedBases
The bases that are allowed at the 5' end of the oligonucleotide. Often, all four bases (A,G,C,T) are allowed. Other times, such as for hybridization probes, a 5' G is not allowed because the G quenches the signal of the fluorescent dye.

Oligo5EndLeftPosition
The most 5' position in the template sequence at which an oligonucleotide can start. This parameter is useful for precisely locating an oligonucleotide in a template sequence.

Oligo5EndRightPosition
The most 3' position in the template sequence at which an oligonucleotide can start. This parameter is useful for precisely locating an oligonucleotide in a template sequence.

Oligo3EndLinker
Analogous to 5' parameter, but at the 3' end of the oligonucleotide.

Oligo3EndModification
Analogous to 5' parameter, but at the 3' end of the oligonucleotide.

Oligo3EndTail
Analogous to 5' parameter, but at the 3' end of the oligonucleotide.

Oligo3EndAllowedBases
Analogous to 5' parameter, but at the 3' end of the oligonucleotide.

Oligo3EndLeftPosition
The most 5' position in the template sequence at which an oligonucleotide can end. This parameter is useful for precisely locating an oligonucleotide in a template sequence.

Oligo3EndRightPosition
The most 3' position in the template sequence at which an oligonucleotide can end. This parameter is useful for precisely locating an oligonucleotide in a template sequence.

Oligo3EndAnalysisLength
The 3' end of a PCR primer is given special consideration because this is where the polymerase attaches. Poor hybridization or secondary structure at this end of the oligonucleotide may have more impact on performance than in other locations of the oligonucleotide. The typical analysis length is the last 5-7 nucleotides of the oligonucleotide.

Oligo3EndGPlusC
The number of Gs and Cs in the last n positions of the oligonucleotide, where n is equal to the Oligo3EndAnalysisLength. Too many Gs and Cs mean the 3' end may hybridize in many locations throughout the genome. Conversely, too few Gs and Cs may mean that the 3' end of the oligonucleotide is hybridized too weakly for proper polymerase interaction. Often, no more than 3 Gs and Cs are allowed.

Oligo3EndDeltaG
A thermodynamic measure of the hybridization strength of the 3' end, where deltaG is the change in free energy. A measure complementary to Oligo3EndGPlusC that in addition to the number of Gs and Cs in the 3' end also takes into account sequence order.

Oligo3EndGCClampLength

The number of contiguous Gs and Cs that end the oligonucleotide. Some researchers feel that ending the oligonucleotide with 2 or 3 contiguous Gs and Cs helps clamp down the 3' end, thereby enhancing the ability of the polymerase to attach to the oligonucleotide-template complex.

Secondary Structure Parameters

OligoAlignMatch

The score given to a Watson-Crick base pairing (C:G or A:T). The value of 1.0 is typical. Watson-Crick base pairings are critical to the performance of an oligonucleotide. The goal is for the oligonucleotide to hybridize to one, and only one, location in the template sequence. The performance of an oligonucleotide is compromised if it has too many Watson-Crick matches with itself (hairpin or self-alignment), with another oligonucleotide (pair alignment), or at another location in the template sequence (mis-priming, non-specific hybridization). While zero matches is the desired hairpin, self-alignment, or mis-priming situation, an oligonucleotide typically performs well even if it has 4 or 5 contiguous matches with itself, with another oligonucleotide, or with another portion of the template sequence.

OligoAlignMisMatch

The score given to a non-Watson-Crick base pairing (A:G; C:T; etc.). A value of –1.0 is typical. This parameter penalizes mismatches in a sequence alignment because mismatches disrupt hybridization due to Watson-Crick matches.

OligoAlinBulgePenalty

Two adjacent nucleotides in a sequence can form Watson-Crick base pairing with two non-adjacent nucleotides of another sequence. This is possible due to the flexibility of the DNA back bone. The unpaired nucleotides of the one sequence bulge out from the helix formed by the paired bases. This situation is heavily disfavored, and so a penalty of –2.0 is typical.

OligoAlignMaxBulgeAllowed

The number of nucleotides allowed between two non-adjacent bases that are paired with adjacent bases. Typically, zero or one bases are allowed. Bulges with more bases are energetically unfavorable.

OligoHairPinMinStemLength

A hairpin structure is formed when a single strand sequence (such as an oligonucleotide) folds back onto itself due to Watson-Crick base pairing. The helix formed by the paired nucleotides is often referred to as a stem. Studies indicate that the minimum number of adjacent Watson-Crick pairings needed to form a helix stem is 2.

OligoHairPinMinLoopLength

The loop of a hairpin structure consists of the unpaired bases of the oligonucleotide that lie between the bases of the stem. Studies indicate that the minimum number of nucleotides in a loop is 3. The rigidity of the DNA back bone prohibits the formation of Watson-Crick base pairing for shorter loops.

OligoHairPinScore

The highest score of all possible hairpin structures. The score reflects the application of the match, mismatch, bulge, and maxbulge parameters. Given the suggested parameter values above, this score is indicative of the longest stem of all possible hairpin structures. Typically, a score of 5 indicates a hairpin structure that impairs the performance of an oligonucleotide. An oligonucleotide that prefers a hairpin structure will not hybridize with the template sequence. The effect of a hairpin is exacerbated because there are typically billions of copies of the oligonucleotide in solution, but only thousands of copies of template. Thus, an oligonucleotide may be much more likely to assume the hairpin structure than the template sequence.

OligoHairPinDeltaG

Some researchers prefer to measure the hybridization strength of hairpin stems using the change in free energy associated with the Watson-Crick matches of the stem. In addition to number of involved bases, change in free energy takes into account the specific bases and the sequence order of the bases.

OligoHairPinTm

Some researchers prefer to measure the consequences of hairpin stems based on the $T_m$ of the stem. This $T_m$ must be sufficiently lower than the $T_m$ of the oligonucleotide when hybridized to its intended target.

OligoPairAlignScore

Helixes can also form when two sequences have Watson-Crick complementarity. This can happen between two copies of the same oligonucleotide or one copy each of two different oligos. Again, an oligonucleotide that prefers to bind to itself or another oligonucleotide will not hybridize with the target sequence.

OligoPairAlignDeltaG

Some researchers prefer to measure the hybridization strength of pair alignments using the change in free energy associated with the Watson-Crick matches of the alignment. In addition to number of involved bases, change in free energy takes into account the specific bases and the sequence order of the bases.

OligoPairAlignTm

Some researchers prefer to measure the consequences of alignments based on the $T_m$ of the alignment. This $T_m$ must be sufficiently lower than the $T_m$ of the oligonucleotide when hybridized to its intended target.

Oligo3EndPairAlignScore

Alignments that involve the 3' ends of both oligos are of special importance because the activity of the polymerase is at the 3' end of the oligonucleotide.

Oligo3EndPairAlignDeltaG

Some researchers prefer to measure the hybridization strength of 3' pair alignments using the change in free energy associated with the Watson-Crick matches of the alignment. In addition to number of involved bases, change in free energy takes into account the specific bases and the sequence order of the bases.

Oligo3EndPairAlignTm

Some researchers prefer to measure the consequences of alignments based on the $T_m$ of the alignment. This $T_m$ must be sufficiently lower than the $T_m$ of the oligonucleotide when hybridized to its intended target.

Sequence Parameters

SeguenceFeature5EndBufferLength

The number of nucleotides that must separate the 5' end of a DNA feature, such as a snp, and the 5' or 3' end of an oligonucleotide. This parameter is useful in precisely locating an oligonucleotide. One purpose is to allow enough sequence between an oligonucleotide and the feature for meaningful molecular analysis. An example is that reliable DNA sequence results typically start some 10 to 20 bases from a sequencing primer.

SequenceFeature3EndBufferLength

The number of nucleotides that must separate the 3' end of a DNA feature, such as a snp, and the 5' or 3' end of a PCR primer. This parameter is useful in precisely locating an oligonucleotide. One purpose is to allow enough sequence between oligonucleotide and the feature for meaningful molecular analysis. An example is that reliable DNA sequence results typically start some 10 to 20 bases from a sequencing primer.

SequenceFeaturePosition5End

The 5' position of a template sequence at which a feature, such as an exon or a SNP, starts. This parameter is useful in precisely locating oligos that target the feature (e.g., A, T, C, but not G at the 5' end).

SeguenceFeaturePosition3End

The 3' position of a template sequence at which a feature, such as an exon or a SNP, ends. This parameter is useful in precisely locating oligos that target the feature (e.g. T, C, G but not A at the 3' end).

Library SequenceAlignScore

The highest alignment score of an oligonucleotide with a library of sequences. This library is typically a compilation of related genes, either from the same organism or from different organisms. If the goal is to amplify a specific gene, then it is undesirable to have substantial Watson-Crick pairings of an oligonucleotide with other genes. Conversely, if the goal is to target a gene family, it is desirable to have substantial Watson-Crick pairings of an oligonucleotide with several genes.

General Methodology

For each entered allelic nucleic acid sequence, an examination region is defined (FIG. 3). An examination region is a segment of nucleotide sequence comprising 1 to R nucleotide positions (bases), where R≦the total number of bases in the sequence, that defines the sequence that must be comprehensively examined. The biochemical model(s) under consideration explicitly or implicitly govern location, length, and purpose. A Sequence Window is a subsegment of examination region comprising 1 to S nucleotide positions, where s≦R. Sequence windows of length s are stepped methodically across the examination region. A sequence window is also defined (FIG. 3). The initial number of nucleotide positions in this window is set to some non-constraining minimum number. The window is placed in a start nucleotide position. The nucleotide sequence contained in the sequence window becomes the first candidate oligonucleotide and so on until all possible candidate reagent oligonucleotides have been determined (FIG. 3, C).

Figure 10:
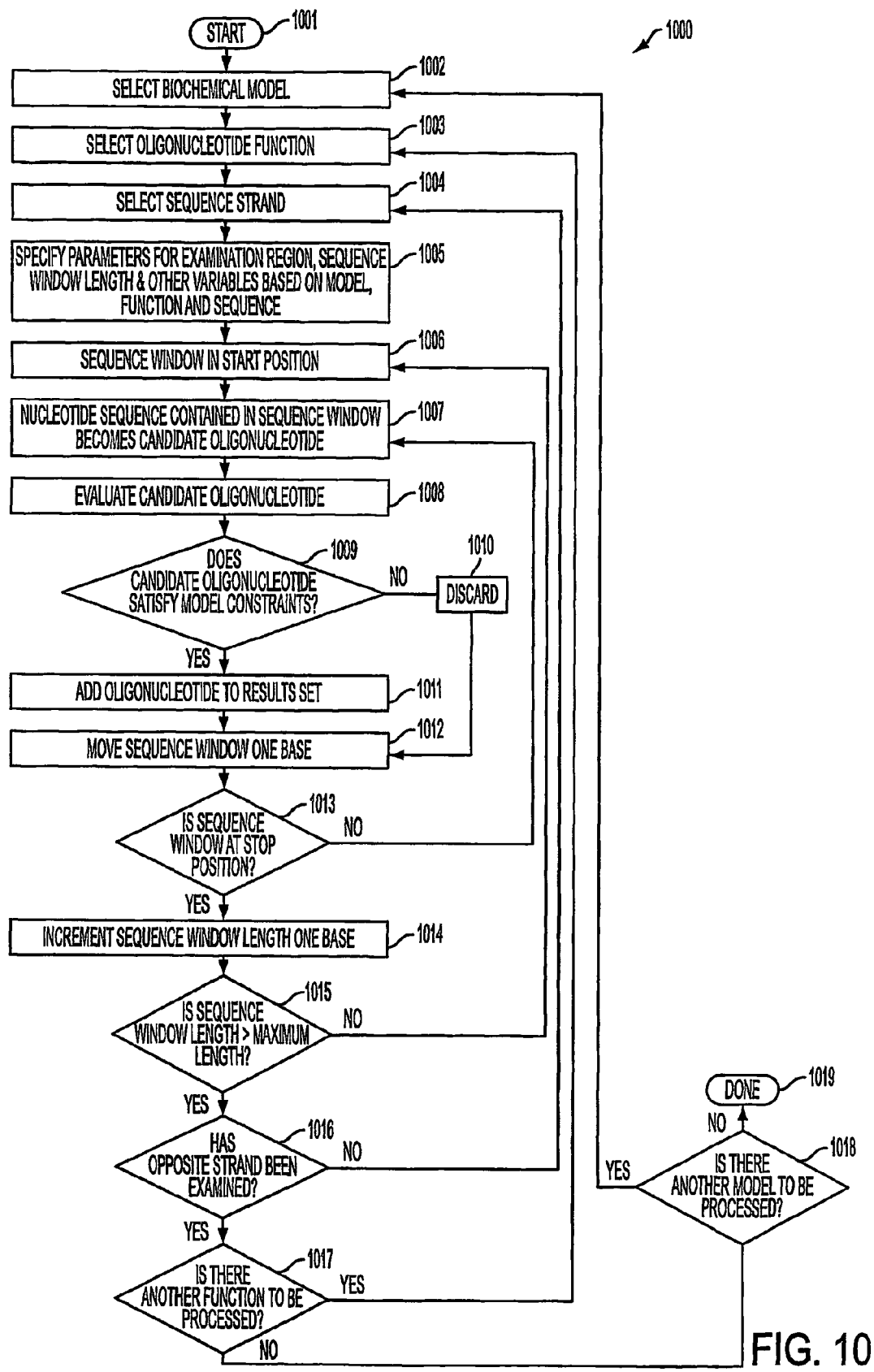
FIG. 10 is a flow chart showing the comprehensive evaluation and examination algorithm of the present invention.

FIG. 10 is a flow chart showing a comprehensive evaluation and examination algorithm. A candidate reagent oligonucleotide (1003) is evaluated (1000) according to the paramaters (1005) of a model that is defined by the particular biochemical (1002) method and function under consideration. If the candidate oligonucleotide (1007) satisfies the constraints of the model (1009), the oligonucleotide is saved for further analysis (1008, 1011). If the candidate fails to satisfy the model, it is discarded (1010).

Next, the sequence window is moved one base position (1012). The window now defines the nucleotide sequence of the second candidate oligonucleotide. This oligonucleotide is evaluated and saved or discarded. This process of evaluation and stepping is continued until the window reaches a stop position (1013, and FIG. 4, A).

The sequence window is now incremented in length by one base position and reset to a new start position (1014). The process of evaluation and stepping is again performed until a new stop position is reached (1001-1013). The process of stepping sequence window length and start position is continued until a maximum window length is attained (1015). This process methodically examines the entire examination region (1016).

Figure 11:
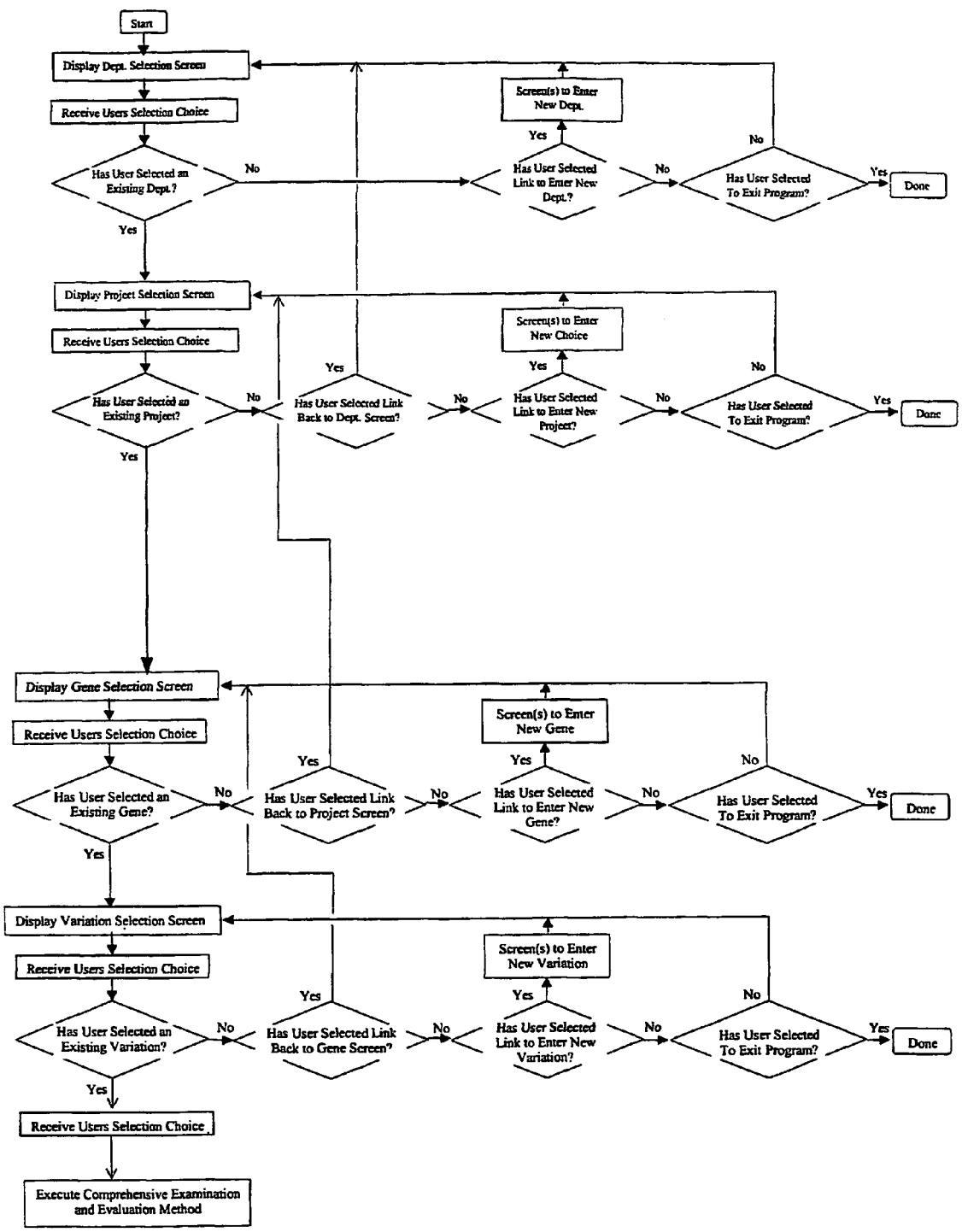
FIG. 11 shows the diagram for ProbeITy™ (Celadon) software package which incorporates the present invention which integrates the algorithm and evaluation process of FIG. 10.

Because DNA is double stranded, and the characteristics of the two strands can differ, this process can be repeated for the opposite strand (1016 and FIG. 4, C & D). It is also repeated for all of the oligonucleotide functions that are required by the specified model (1017, compare FIGS. 4, A & B to C & D). This process can also be repeated for more than one molecular biology model per method and one or more methods (1018). It can also be repeated for more than one genetic variation. Using a graphical user interface integrated into the software than carries out the invention, a user navigates between fields and screens and may repeat the process for another target nucleic acid sequence, another target feature of a target nucleic acid sequence, another biochemical method with the same or different target nucleic acid sequence, or any combinations thereof (see FIG. 11).

If batch processing is to be performed without user intervention, selection criteria typically must be specified so that typically a single oligonucleotide is chosen for each oligonucleotide function otherwise a user may opt to terminate the program (1019).

Examination Region

Each molecular biology method will have associated with it one or more Examination Regions, e.g., a segment of nucleic acid adjacent or flanking on either side to the polymorphic region. There is typically one examination region for each oligonucleotide function (e.g., as a primer, hybridization probe, or antisense nucleotide, etc.). Typically, the order of processing of the oligonucleotide functions, and thus examination regions, is important. Examination regions can be sorted into one or more priority classes whereby the one or more examination regions in a higher priority class are processed before the one or more examination regions of lower priority classes. Within priority class, examination regions may be processed in any order. The examination region associated with a lower-priority oligonucleotide function may depend on the specific oligonucleotides chosen for higher-priority functional classes. The examination region need not be specified explicitly by a model, but may be implicit to the model.

Sequence Window

The parameters of a specified biochemical model are constraints that must be satisfied. Let the finite number of oligonucleotides that satisfy these constraints be the "solution set" or "results set" (the term is used herein interchangeably). Oligonucleotides in the solution set will range in length from some minimum length ($L_{min}$) to some maximum length ($L_{max}$). However, the value of $L_{min}$ and $L_{max}$ are not known before hand.

Because of this, a sequence window (FIG. 3, feature B) is defined that ranges in length from $W_{min}$ to $W_{max}$, where typically $W_{min} \leq L_{min}$ and $W_{max} \leq L_{max}$. Thus, $W_{min}$ and $W_{max}$ are non-constraining in that any shorter or longer window lengths generate only candidate oligonucleotides that fail to satisfy model constraints. $W_{min}$ may be greater than $L_{min}$ and $W_{max}$ may be less than $L_{max}$ to speed computation time if only non-optimal oligonucleotides of the solution set are not evaluated. Typically, $W_{min}$ and $W_{max}$ are chosen such that qualifying candidates begin appearing at window lengths several positions longer than $W_{min}$ and stop appearing several positions short of $W_{max}$. Due to fast computational speeds of modern computer microprocessors this excess examination typically is not onerous. A person having ordinary skill in the art would be able to determine desired settings of $W_{min}$ and $W_{max}$ without undue experimentation.

Biochemical Models

Model variables can include all variables that are well known in the art to influence performance of oligonucleotide annealing, melting, hybridization, and stability. For a single oligonucleotide, this includes but is not limited to $T_m$ (melting temperature in Celsius), 3' stability, length, GC-content, 5' and/or 3' self complementarity and propensity to form secondary structures with itself, the base at 5' position, number of Gs and Cs at the last five 3' positions, avoidance of runs of repeated nucleotides or nucleotide types (e.g., purine or pyrimidine), synthesis chemistry, and secondary structure. For more than one oligonucleotide, variables can include pairwise complementarity. For PCR products, variables can include product size and product $T_m$.

$T_m$ is typically a critical constraining variable. Many methods specify a minimum and maximum $T_m$ that defines a narrow range. A number of methods, and preferably the nearest neighbor model, can be used to calculate oligonucleotide $T_m$. The nearest neighboring model depends on experimentally derived values.

$T_m$ can be calculated for both perfect matches and mismatches. A perfect match arises when an oligonucleotide has perfect Watson-Crick base pairing with its complementary target. A mismatch is when there are one or more mismatches between an oligonucleotide and its complementary target. Currently, nearest neighbor values are available only for single base mismatches. Estimation of mismatch $T_m$ is especially relevant to allele-specific hybridization probes, where an important selection criterion is to maximize the difference between perfect-match $T_m$ and mismatch $T_m$ ($\Delta T_m$). Allelic discrimination typically improves as $\Delta T_m$ increases. Perfect match $T_m$ is typically higher than mismatch $T_m$.

Another important model variable is the chemistry used to synthesis oligonucleotides. Phosphoramadite chemistry is standard. In addition, Applied BioSystems, Inc. manufactures a PropyneT chemistry that is marketed as Turbo TaqMan™. PropyneT is a thymidine derivative that increases the nearest neighbor $T_m$ by 1.0° C. for every thymidine in the oligonucleotide. PropyneT improves the performance of allele-specific hybridization probes when the probe has a GC content of about 65% or less because PropyneT probes tend to be shorter and attain the targeted minimum $T_m$ and shorter probes tend to yield higher predicted $\Delta T_m$. Higher predicted $\Delta T_m$ typically yield increased allelic discrimination. Derivatives for especially adenine, but also guanine and cytosine, that increase hybridization strength, would be an important means to further improve allelic discrimination by decreasing allele-specific probe length.

A final important variable well known in the art is secondary structure. Secondary structure refers to the stem and loop shapes that oligonucleotides assume due to self-complementarity. Stems are regions of self-complementarity and loops are regions of non-self complementarity. It is known in the art that that a stem and loop structure that looks like a clamp, as embodied in molecular beacons, enhances allele-specific hybridization.

Constraints Imposed by Genetic Variation

An important consideration in assay design for genetic diversity is that oligonucleotides are constrained primarily by the sequence context of the targeted polymorphism or other target feature. Further, choice of forward and reverse PCR primers can be constrained by the need to minimize PCR product length. These two factors can greatly limit examination regions. A biochemical model that has many variables with stringent parameters may frequently generate an empty solution set.

Further, it is important to realize that simple models that take into account only two or three variables have performed adequately in some labs. The present invention is demonstrated using a four variable model that for the 5' nuclease assay has a success rate of >90%. Models that take into account additional variables may improve the success rate of assay designs.

For model building, the sequence constraints of targeting genetic variation and the success of simple models suggest a forward selection process. That is, to first investigate one or two additional variables that are likely to have substantial impact on performance.

Process

Experience in designing 5' nuclease assays has led to the definition of a set of tasks and an ordering of these tasks. Further, it has led to the definition of a biochemical model with default parameter values that rarely need to be change. Methodically following the set of ordered tasks and using the default parameters results in a successful assay design >90% of the time.

The present invention simplifies this process by reducing it into software via a user interface wizard. This interface methodically leads users through the defined process, thereby performing for the user repetitive and time-consuming tasks. Typically, the user merely needs to use the mouse to point and click through the series of screens. Only rarely will the user need to change parameter settings or make other kinds of manual interventions.

The graphical user interface presents to the user the oligonucleotides in the solution set, typically sorted by one or more variables in the model. The user then can scroll among these lists so as to select their preferred oligonucleotides. Typically, these will be oligonucleotides at, or near, the top of the list. The user interface allows only one oligonucleotide to be selected for each functional category and oligonucleotides must target the same strand.

Max of the Min Selection Criteria

For a given oligonucleotide function, there typically are at least several candidate oligonucleotides within each solution set. Further, the user typically has a solution set from more than one model to choose from. Because of this it is useful to define selection criteria (or ranking parameters). Selection criteria are a convenient guide if the user manually selects an oligonucleotide from a solution set. Selection criteria are a necessity if the user desires assay designs to be generated automatically, as would be the case with batch processing of many genetic variations.

Within solution sets, the selection criteria could be to pick the oligonucleotide that appears at the top of the sorted list, assuming the list is sorted with those oligonucleotides having the most optimal characteristics at the top. To choose among more than one model, the model should be chosen for which the oligonucleotides for each function exhibit the most preferred characteristics.

The present invention specifies a selection criteria set for the special case in which two or more allele-specific hybridization probes are being compared among two or more models. The strategy is to select for each model the probe with the worst characteristics. The probe among these that has the best characteristics specifies the model that should be chosen.

EXAMPLES

Oligonucleotide Selection for the Applied Biosciences, Inc. "TaqMan™" Assay and SNP Analysis The preferred embodiment in this example is the 5' nuclease method. In this method there are typically four oligonucleotides: 2 allele-specific hybridization probes, 1 forward PCR primer and 1 reverse PCR primer. The two allele-specific hybridization probes constitute one priority class and the forward and reverse PCR primers constitute a second priority class. The allele-specific hybridization probes have higher priority than the PCR primers so that the PCR primers do not overlap the allele-specific hybridization probes.

The alleles of the genetic variation, for which allele-specific hybridization probes are needed, typically can be processed in any order. Once allele-specific hybridization probes are chosen, the forward and reverse PCR primers can typically be processed in any order. In this model, the examination regions for the forward and reverse PCR primers depend on the exact oligonucleotides chosen as allele-specific hybridization probes.

TABLE 1A

Standard and Propyne T Chemistry Models and Default Parameter Values for the Allele-Specific Hybridization Probes of the 5' Nuclease Method

|  | Standard | PropyneT |
|---|---|---|
| 5' Position | No G | No G |
| Min $T_m$ | 68.0° + GC % factor* | 68.0° + GC % factor |
| Max $T_m$ | 72.0° | 72.0° |
| Open Positions | Middle Third | Middle Third |
| Nearest Neighbor Values | Unified | Unified + 1.0*(#Ts) |
| T Synthesis Chemistry | Phosphoramadite | 5-propyne-2'deoxyuridine |
| $\Delta T_m$ | Calculate | Calculate |

GC % factor is to increase Min $T_m$ (and Max $T_m$ if necessary) some amount, typically about 0.5°-1.0° C. every 10% above 50%.

Figure 5A:
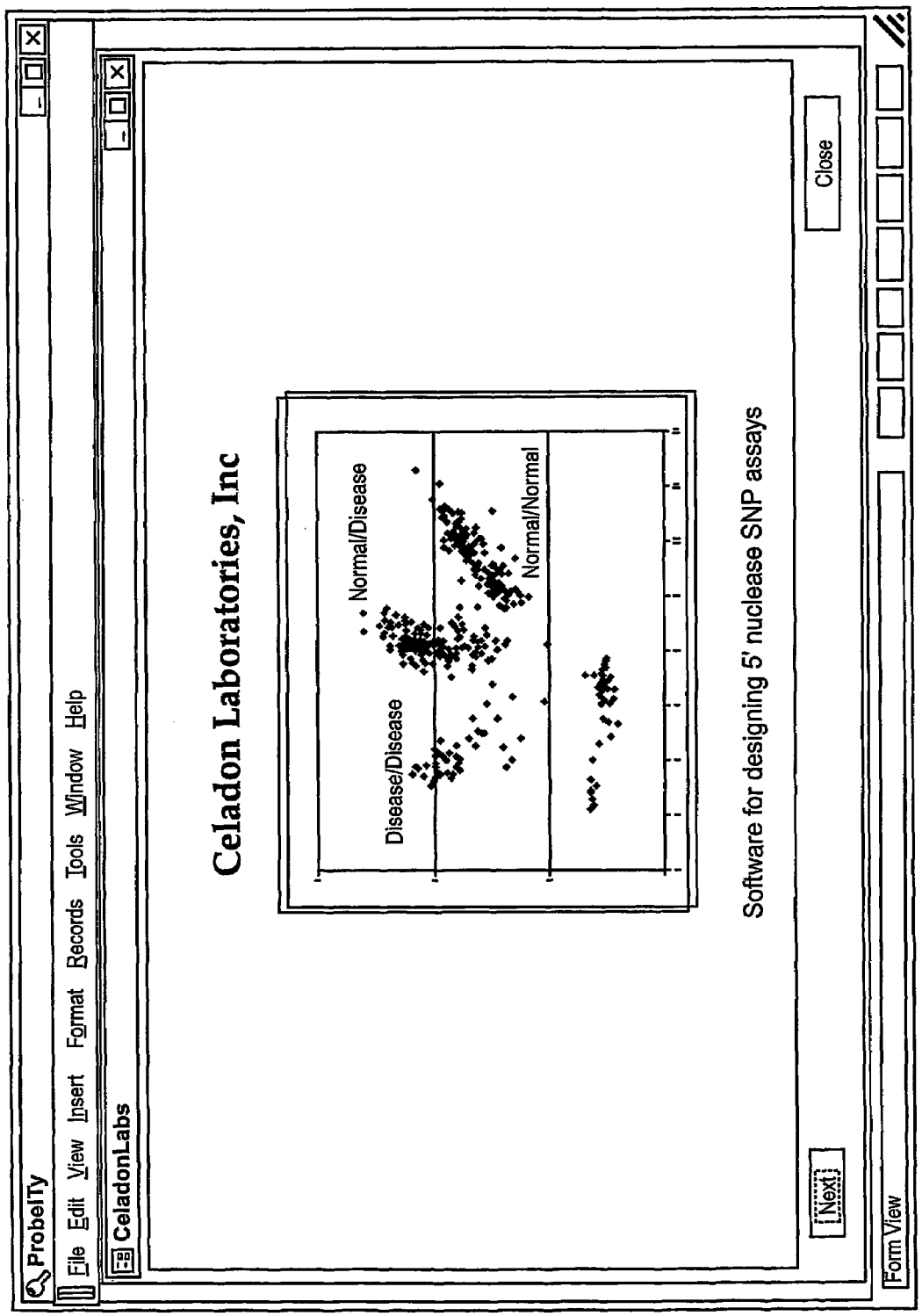
Figure 5B:
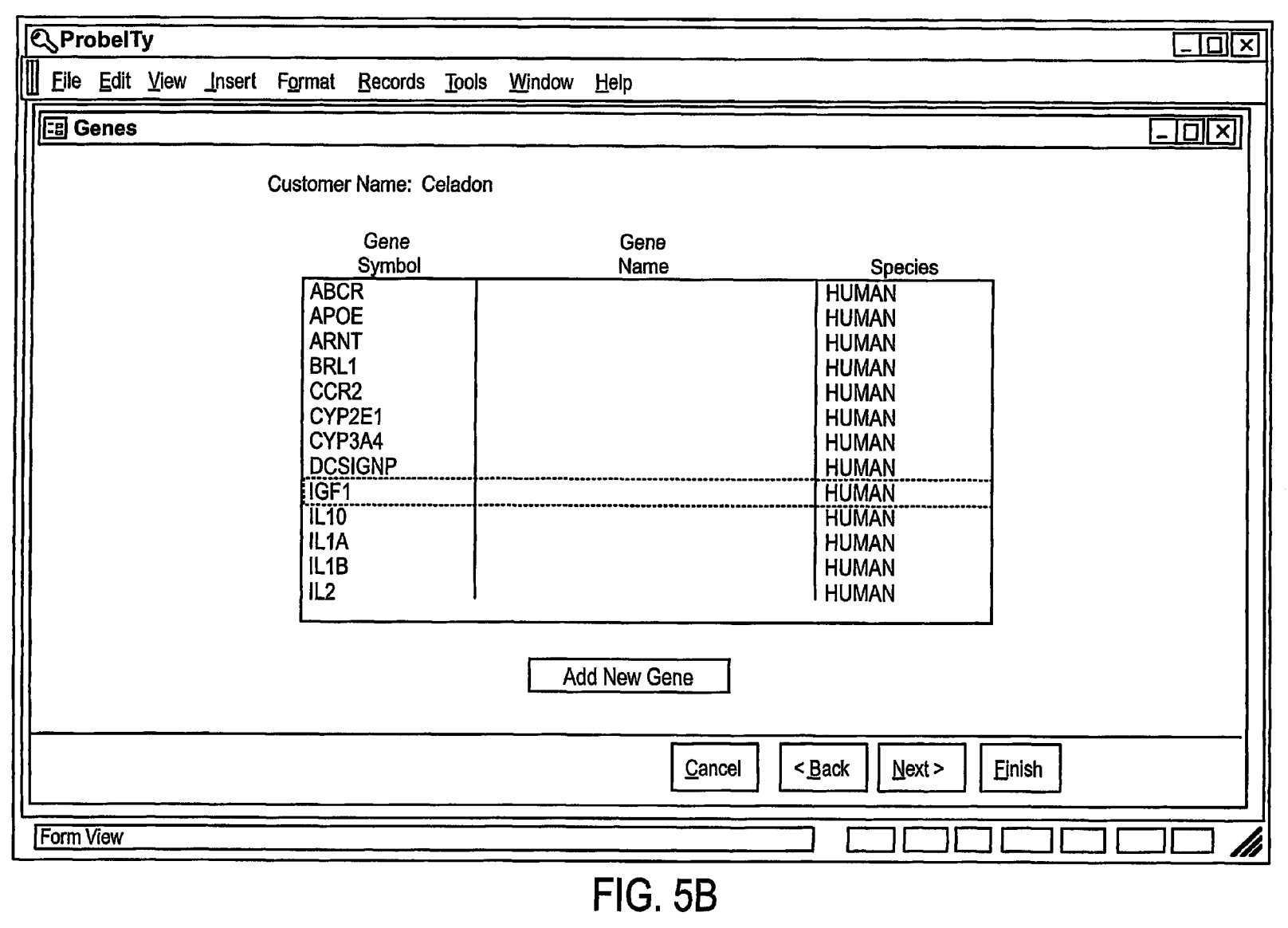
Figure 5D:
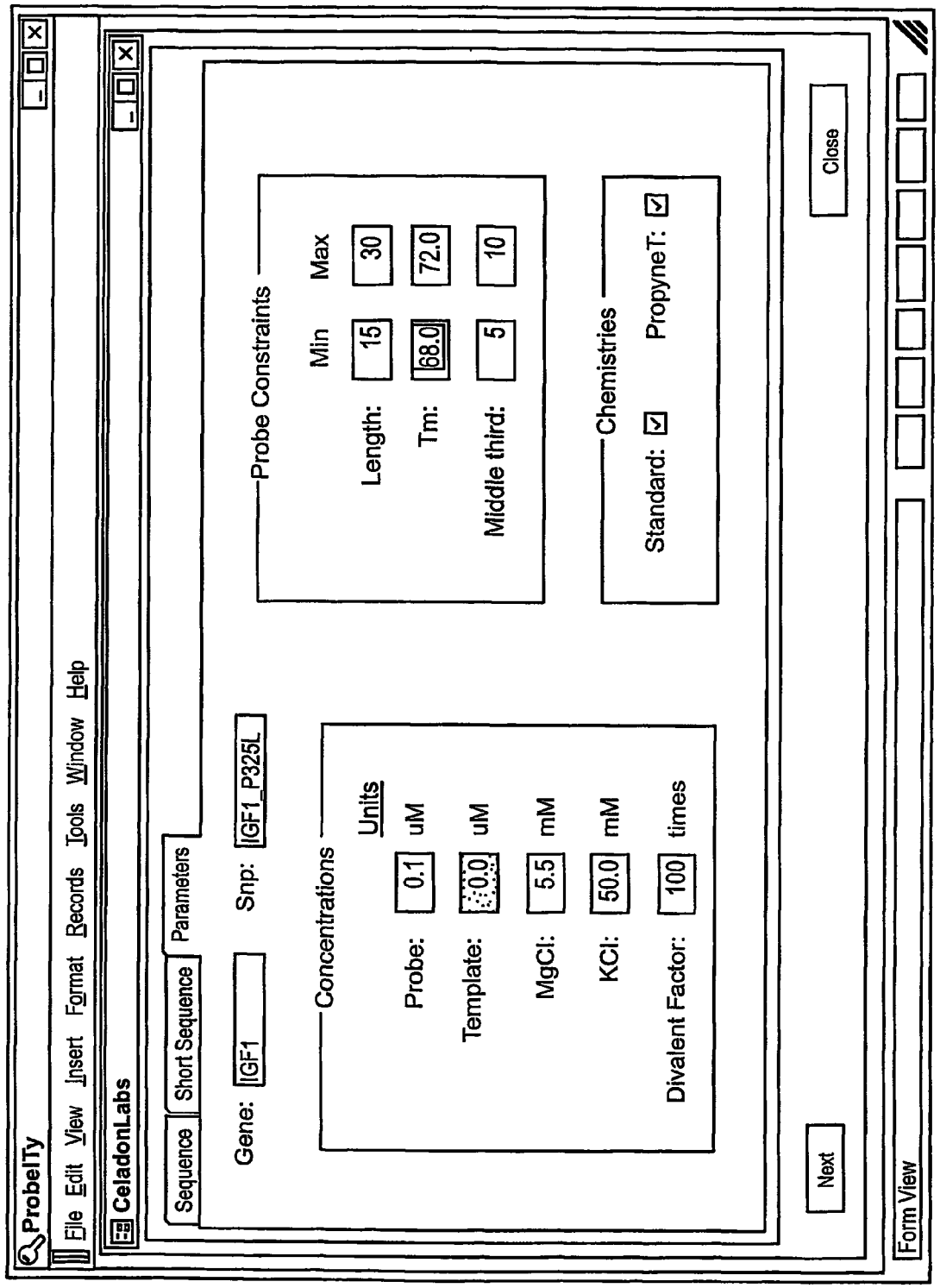
FIG. 5D shows the parameter selection screen for the probe model with default values. Default parameter values that rarely need to be adjusted are shown. On the left of the screen shot of FIG. 5D are the variables of the biochemical model for which the user can enter parameter values. On the right, the probe constraints box contains input boxes for $W_{min}$, $W_{max}$, MinTm and MaxTm. The chemistries box has check boxes for selecting one of two biochemical models. The choices shown are standard phosphoramadite chemistry and PropyneT chemistry (see Table 1). The difference between the two models are the values used to calculate $T_m$.
Figure 5E:
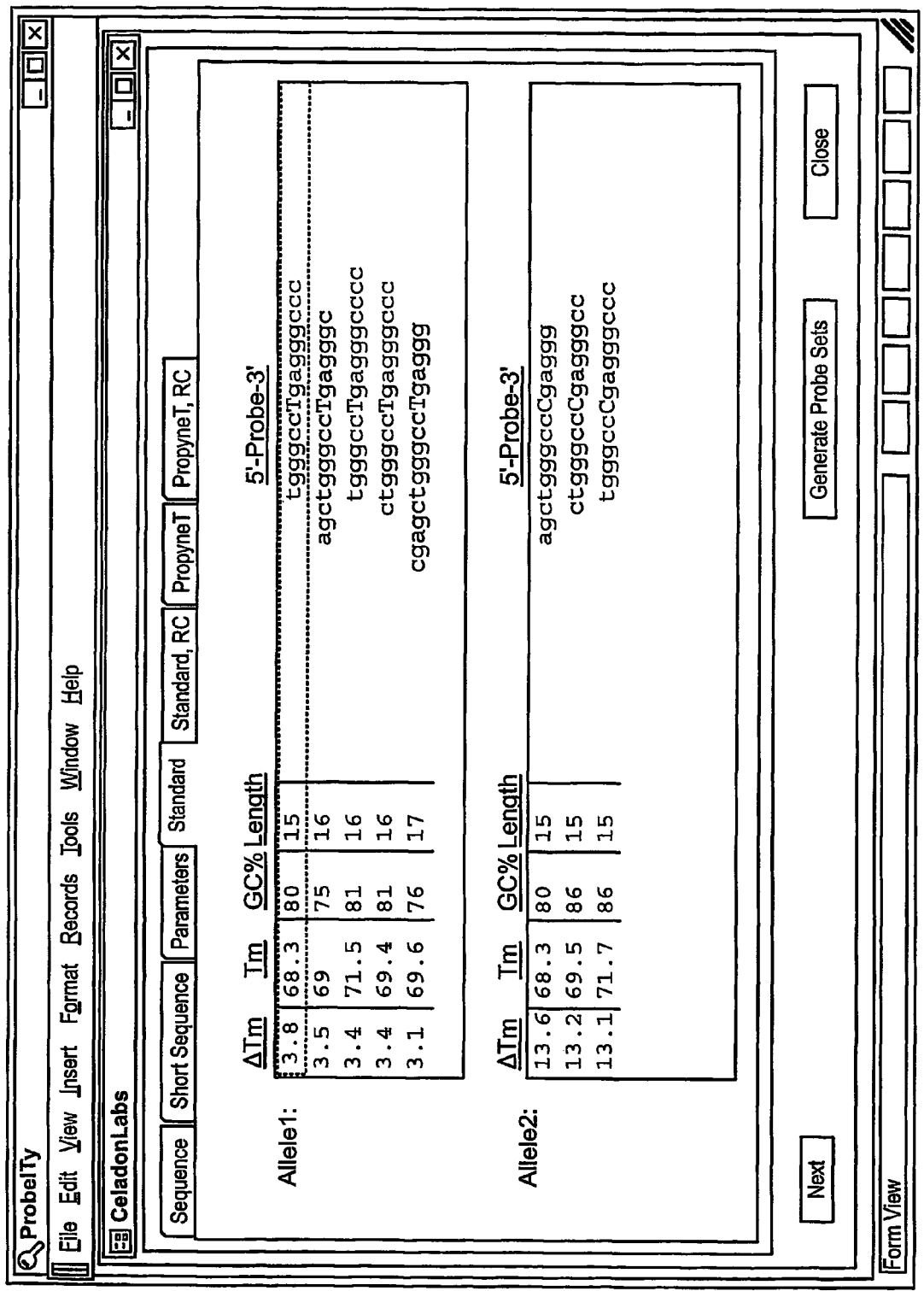
FIG. 5E (SEQ ID NOS 8-15, respectively in order of appearance) shows a results screen where the saved (within exclusion parameter constraint values) versus discarded (outside exclusion parameter constrain values) reagent oligonucleotide sequences are sorted by $\Delta T_m$ for the standard chemistry of the sense strand.
Figure 5F:
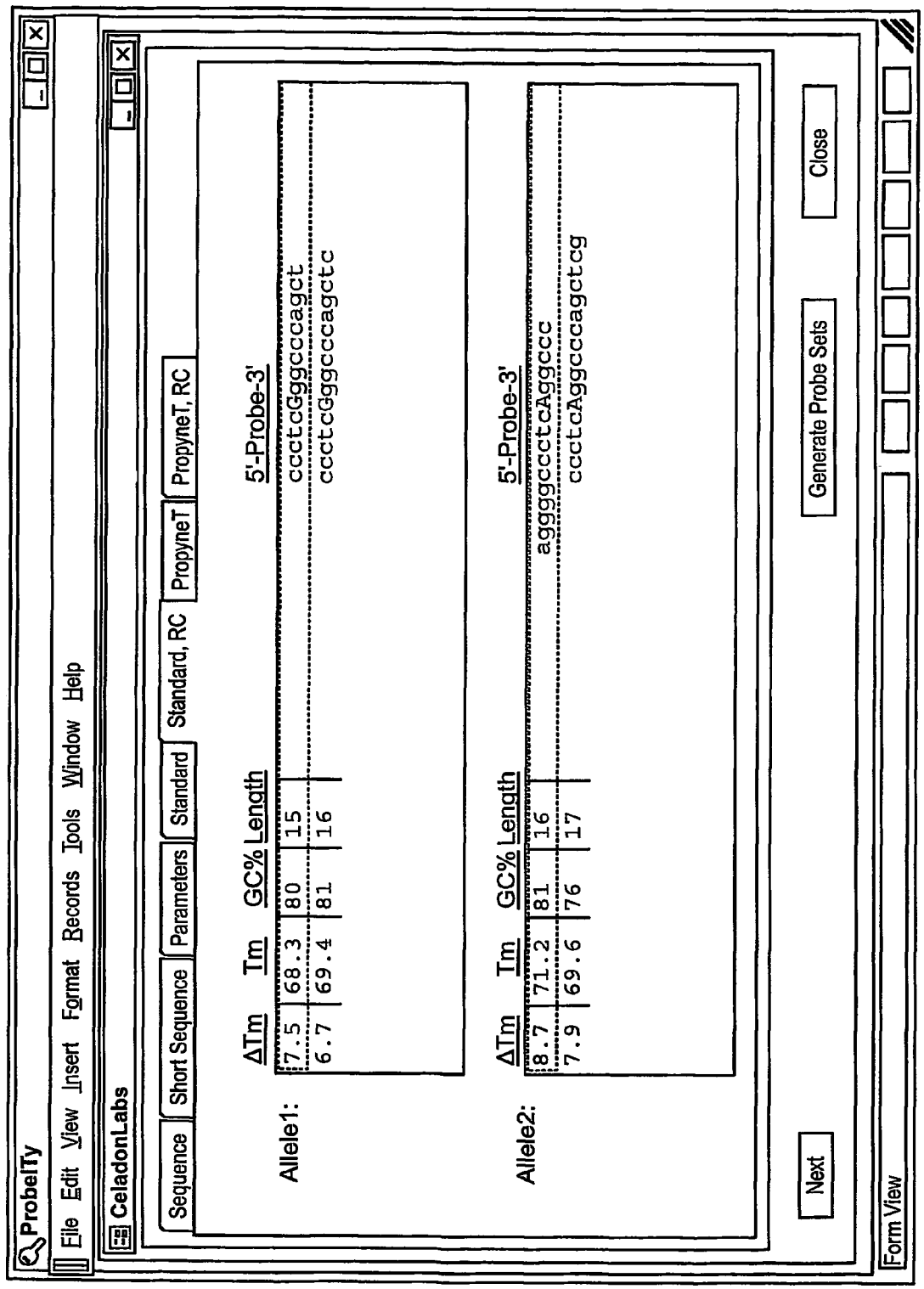
FIG. 5F (SEQ ID NOS 16-19, respectively in order of appearance) shows a results screen where the saved (within exclusion parameter constraint values) versus discarded (outside exclusion parameter constrain values) reagent oligonucleotide sequences are sorted by $\Delta T_m$ for the standard chemistry of the antisense strand.
Figure 5G:
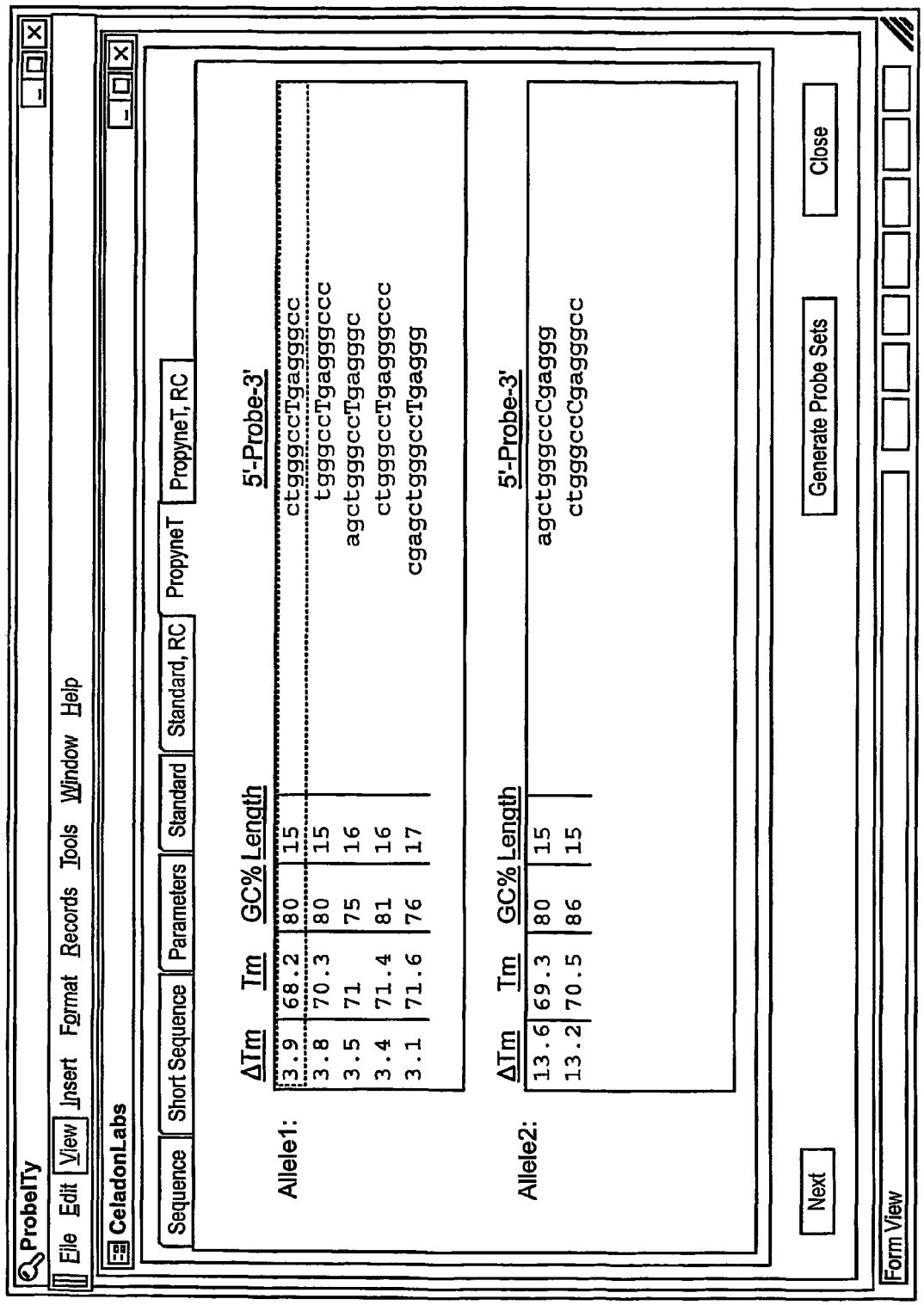
FIG. 5G (SEQ ID NOS 20-26, respectively in order of appearance) shows a results screen wherein the determined oligonucleotides are sorted by $\Delta T_m$ for the PropyneT chemistry of the sense strand.
Figure 5H:
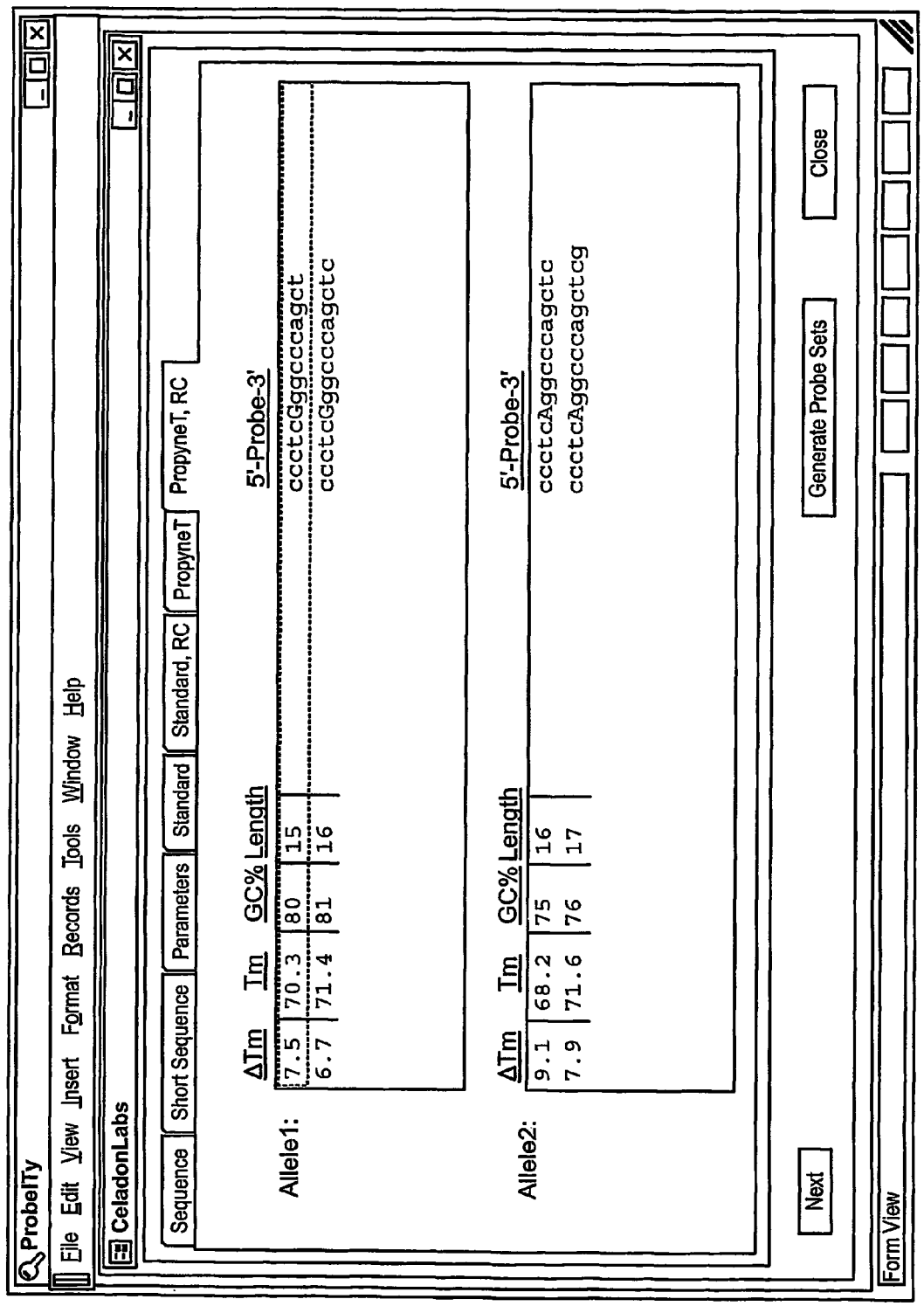
FIG. 5H (SEQ ID NOS 27-30, respectively in order of appearance) shows a results screen wherein the determined oligonucleotides are sorted by $\Delta T_m$ for the PropyneT chemistry of the sense strand.

Turning to FIG. 5D, a set of potential oligonucleotides are generated for an entered allelic nucleic acid, when a user hits the next button. This operation initiates the comprehensive examination and evaluation algorithm. The first steps of this process are depicted in FIG. 4A-D. These steps address the examination regions of the two allele-specific hybridization probes, which are the first priority.

In FIG. 4, A, a portion of the examination region of the sense strand for allele C is depicted where the variable base is in upper case and all other nucleotide positions are in small case. Also depicted are all possible oligonucleotides of $W_{min}=15$ for which the variable base lies in the middle third of the oligonucleotide. This later constraint is the default parameter setting of the open positions variable of the 5' nuclease model. Mismatches in the middle of an oligonucleotide tend to disrupt hybridization more than mismatches towards either end.

With reference to the numbering system of FIGS. 2, A & B, the Open Positions constraint defines positions 6-10 of the sequence window as the Open Positions. In turn the Open Positions parameter dictates that the first start position in the examination region be position −5. The variable position is paired with the sequence window position 6, which is the first open position. In this location, the sequence window defines the first candidate oligonucleotide to be the sequence having positions 5 to 9 of the examination region. This candidate is evaluated with respect to the first 5' nuclease model, and saved or discarded.

The sequence window is then incremented one base 5' so as to pair the variable base with the next open position, which is position 7. In this location, the sequence window defines the second candidate oligonucleotide as positions −6 to 8 of the examination region. This candidate is evaluated with respect to the 5' nuclease model and saved or discarded. This process is repeated for open positions 8, 9 and 10. The open positions dictate the stop position in the examination region to be position −9.

The sequence window is now incremented one base to length 16 (not shown), and the process examination and evaluation is repeated until the new stop position is reached. The process of incrementing the sequence window is repeated until the window length is equal to $W_{max}=25$. By this method, the first examination region is comprehensively examined, and all oligonucleotides in the solution set are identified.

The comprehensive examination and evaluation described above is repeated for the second examination region corresponding to the second allele-specific hybridization probe (FIGS. 4A&C vs B&D). It is also repeated for both strands (FIGS. 4A&B versus C&D), and for both biochemical models (not shown).

The solution sets are listed in FIGS. 5E-H. As can be seen, the oligonucleotides in each solution set are sorted in descending order for the $\Delta T_m$ variable. Other pertinent information, such as $T_m$, GC %, length, and oligonucleotide sequence, is shown. In the present system, the selection criterion is to maximize $\Delta T_m$. Thus, the results that the user first sees are for the antisense strand and the PropyneT chemistry model. This is because the minimum $\Delta T_m$ between allele-1 and allele-2 for this model is 7.5. The other pairwise minimum $\Delta T_m$s are 7.5, 3.9 and 3.8. If the solution sets are deemed inadequate, the user can select to return to the parameters screen, change parameters, and re-run the comprehensive examination and evaluation algorithm.

Figure 5I:
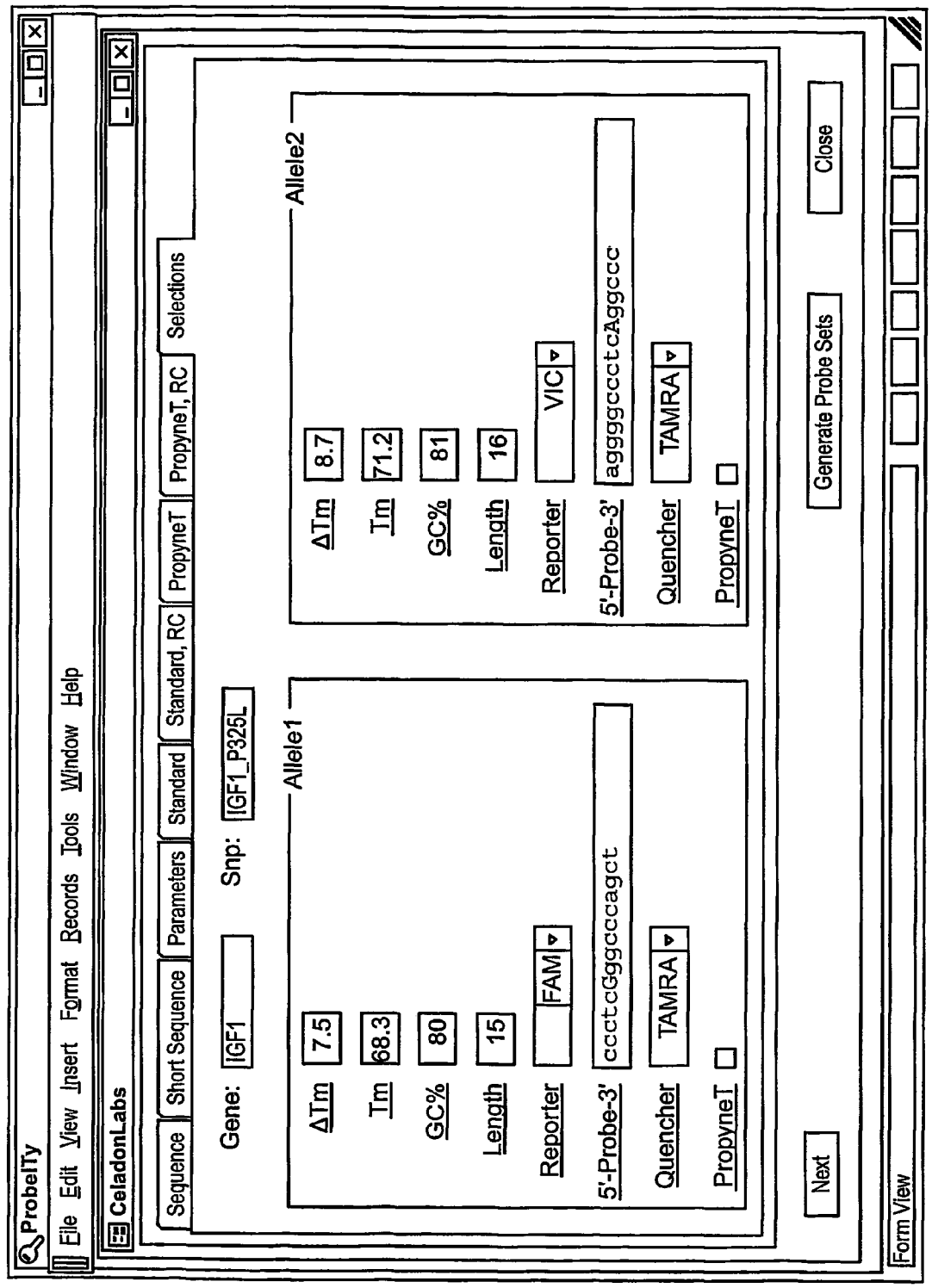
FIG. 5I (SEQ ID NOS 31 & 32) shows Probe results screen with oligonucleotide reporter and quencher defaults.

FIG. 5I depicts the users selections. Before display, the selections are evaluated to confirm that the user has made a selection for each required oligonucleotide and that the oligonucleotides target the same strand. The user has the choice only of reporter and quencher dyes, as all other values are calculated. The default values of the reporter and quencher dyes are shown, and these rarely need to be changed. It is possible to select an unmodified oligonucleotide, that is, to select 'None' for the reporter or quencher.

Figure 5J:
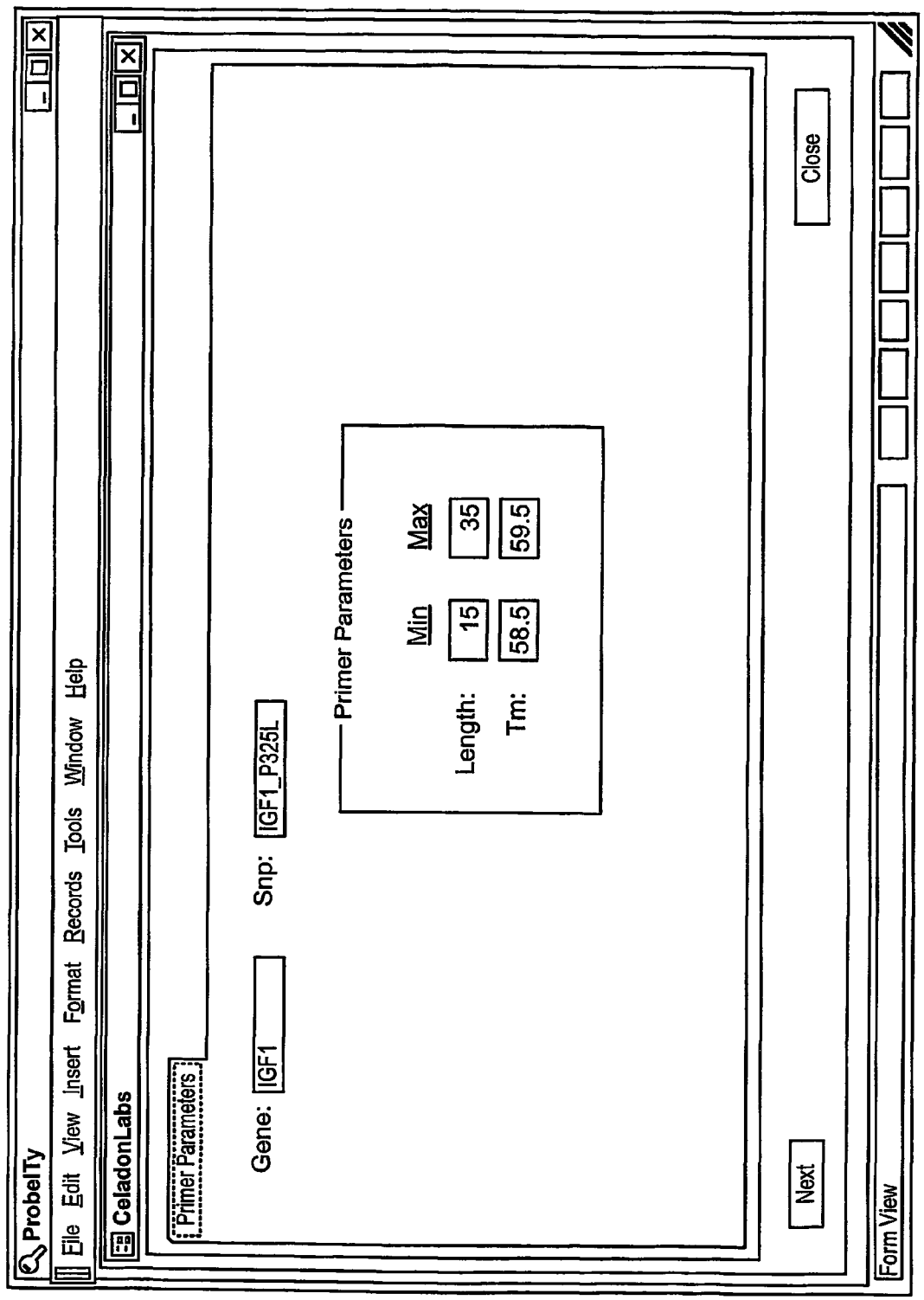
FIG. 5J shows a screen for parameter selection and default values.

Clicking on the Next button of the probe selections screen leads to the primer parameters screen (FIG. 5J). Here the user can enter $W_{min}$, $W_{max}$, Min-$T_m$ and Max$T_m$ values. The defaults are shown, and these rarely need to be adjusted.

The examination region of the forward PCR primer is defined to end one base 5' of the most 5' position of the hybridization probes. The beginning of the examination region is either the most 5' position of the inputted flanking sequence, or position −100 relative to the variable position, whichever is reached first. The latter value is for convenience only and could be larger or smaller. The examination region of the reverse PCR primer is defined in an analogous manner.

Figure 5K:
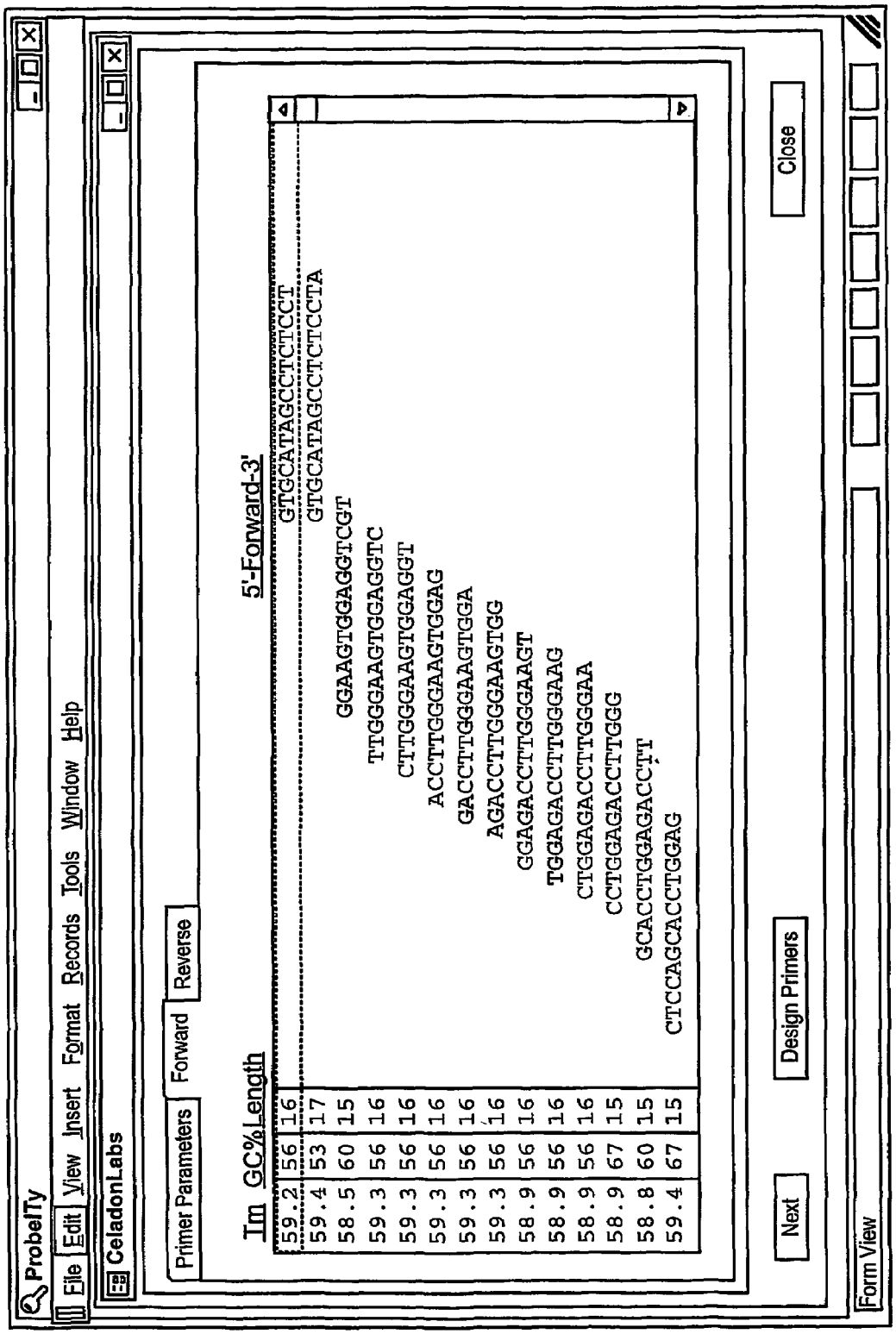
FIG. 5K (SEQ ID NOS 33-46, respectively in order of appearance) shows the results screen for forward PCR primer with primers tiling to the left away from targeted variation.
Figure 5L:
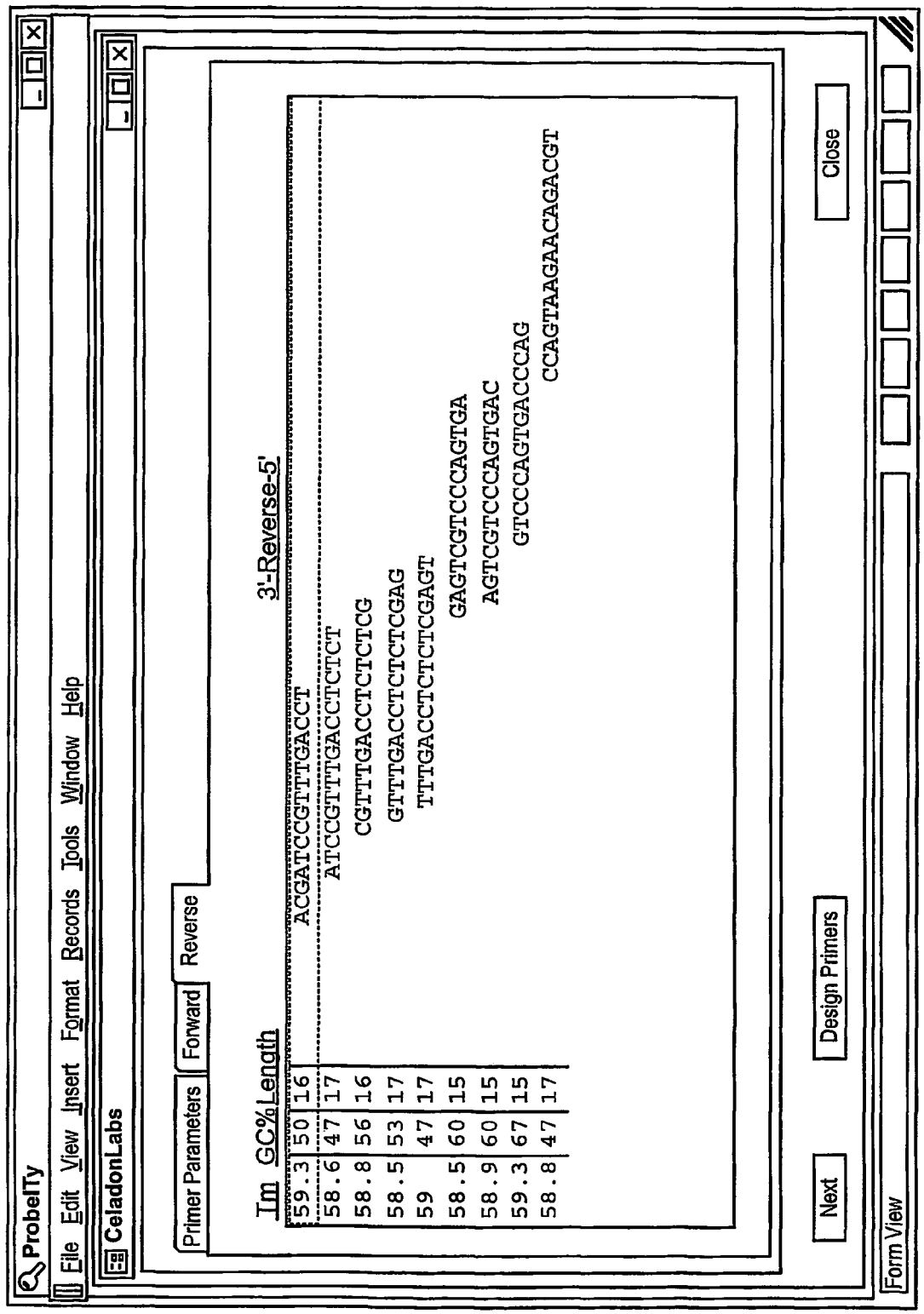
FIG. 5L (SEQ ID NOS 47-55, respectively in order of appearance) shows the results screen for reverse PCR primer with primers tiling to the right away from targeted variation.

FIG. 5K shows the solution set for the forward primer and FIG. 5L show the solution set for the reverse primer. The forward primers are displayed 5'→3' with the oligonucleotides closest to the variable site at the top of the list, and are aligned with the 5' flanking sequence. The reverse primers are displayed 3'→5' also with the oligonucleotides closest to the variable site at the top of the list, and are aligned with the 3' flanking sequence.

Figure 5M:
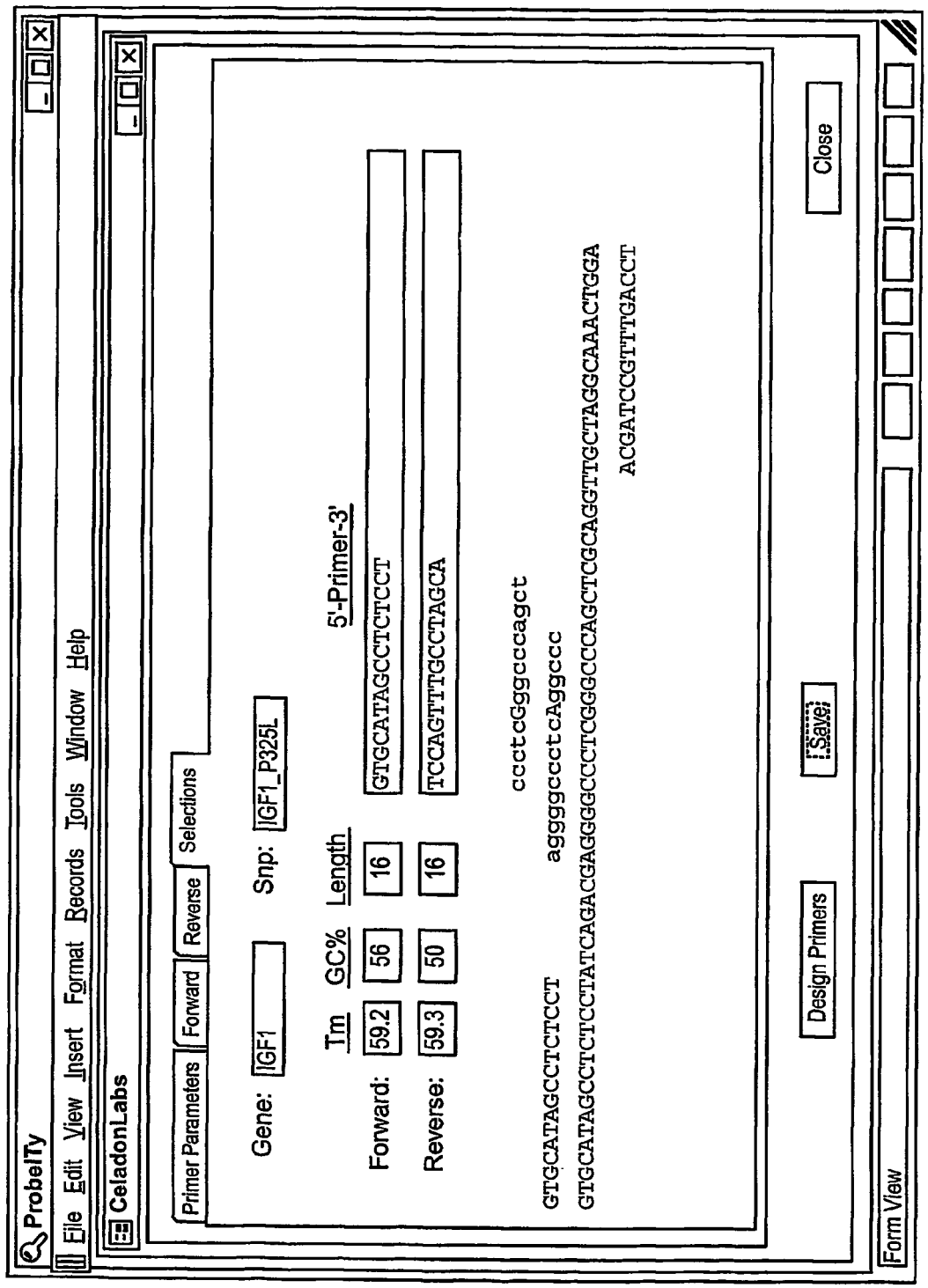
FIG. 5M (SEQ ID NOS 56-60) shows the results screen for primers and showing primers and probes on inputted sequence. The targeted sequence is SEQ ID NO: 60; the forward primer is SEQ ID NO: 56; the reverse primer is SEQ ID NO: 57; and the two central oligonucleotides are SEQ ID NO: 58 (upper) and SEQ ID NO: 59 (lower).
Figure 5N:
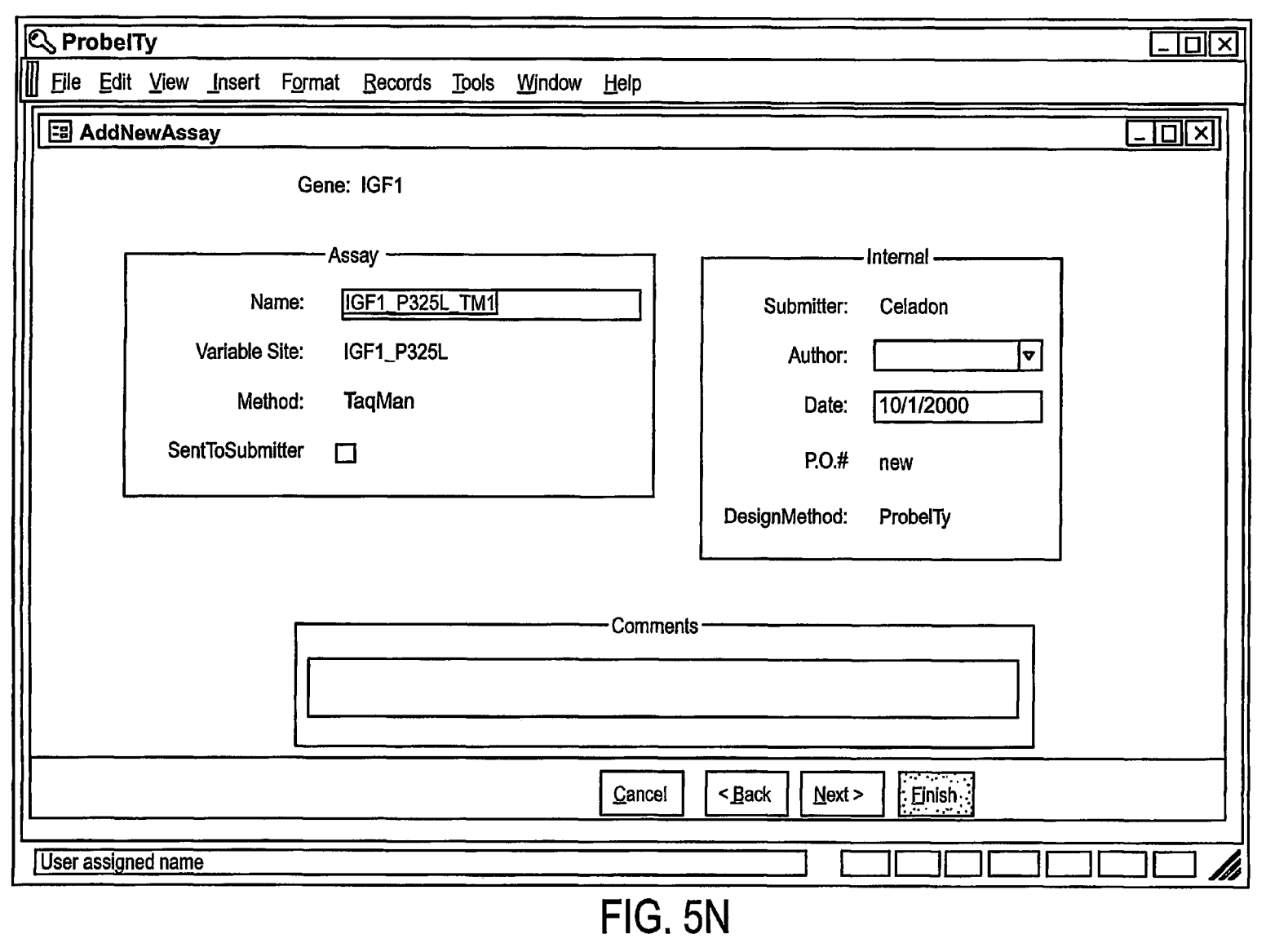
Figure 50:
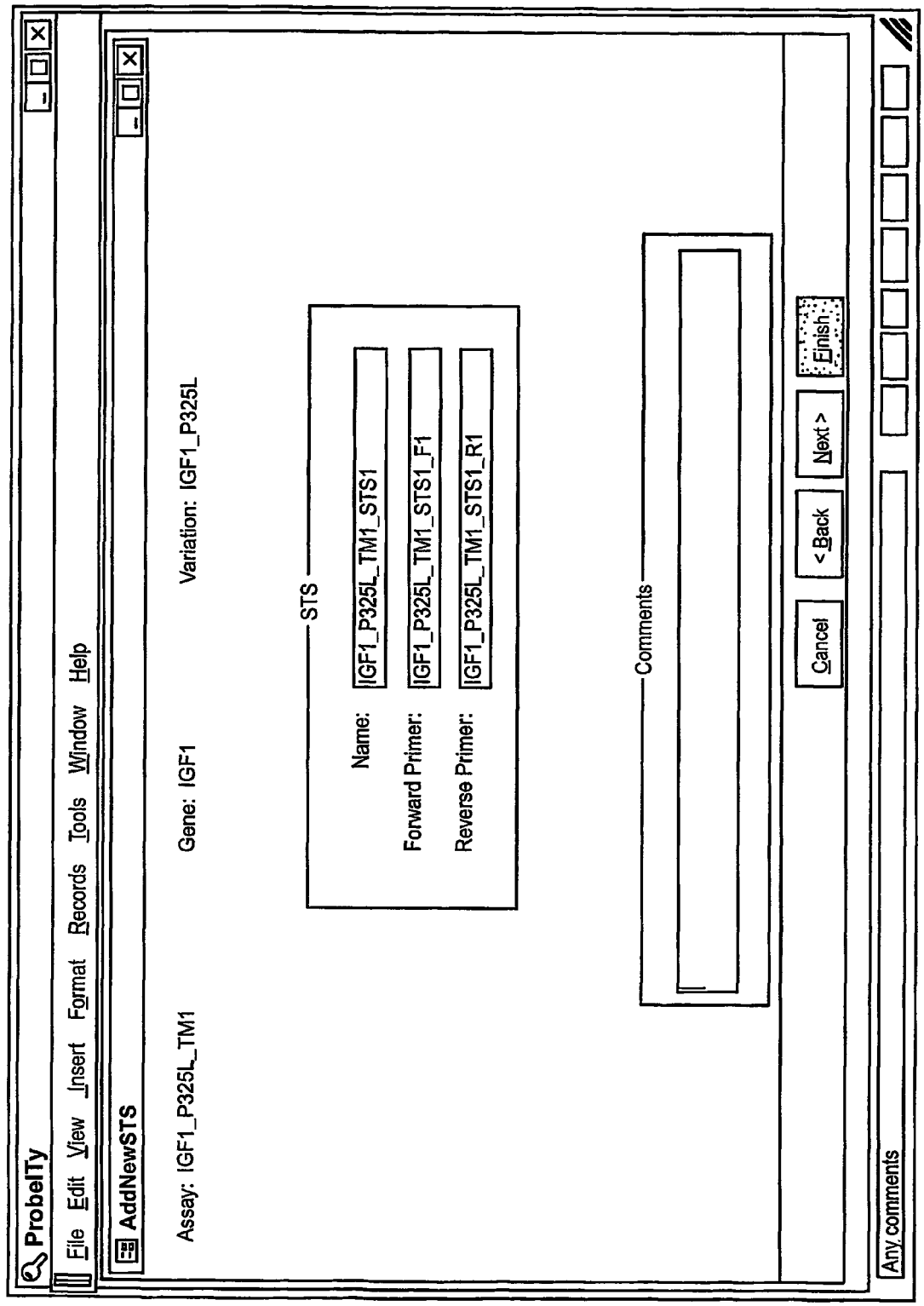

Primer selections are depicted in FIG. 5M. Also depicted are the selected allele-specific hybridization probes and PCR primers aligned with the nucleotide sequence flanking the variable position. The user has no design choices here as all values are calculated. Clicking on the Save button leads the user to a screen to enter a name for the assay and other information (FIG. 5N). The default name follows the scheme of naming the assay based on the name of the gene in which the variation lies, the name of the variation, and a shorthand name for TaqMan, which is "TM". Since this is the first TaqMan assay to be designed, it is designated as 1. The final screen allows the user to select names for the PCR primer set and each PCR primer.

Figure 6A:
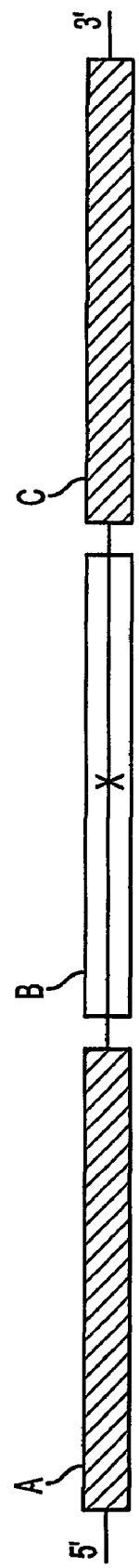
FIGS. 6A-6F show method specific forward and reverse primer annealing sites and allele specific probe sites relative to a polymorphic site. In all of these figure the areas indicated by shading show the region of the target nucleic acid where a reagent oligonucleotide is complimentary and would optimally bind as a primer or probe.
Figure 6B:
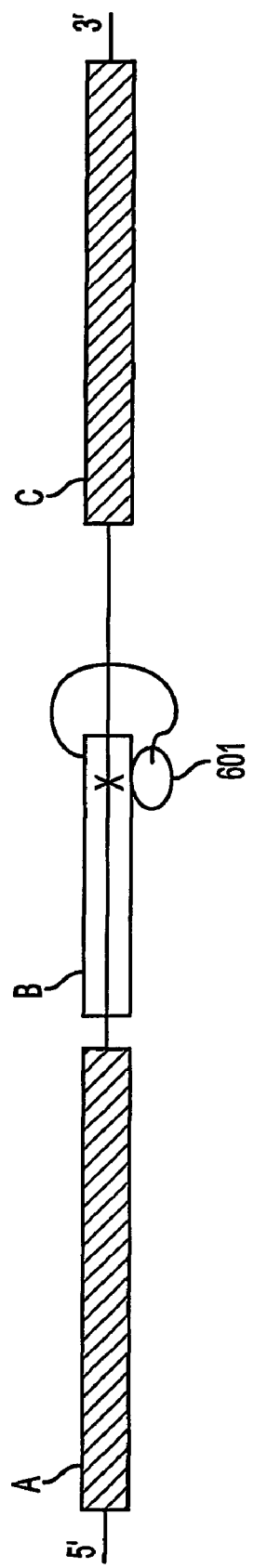
Figure 6C:
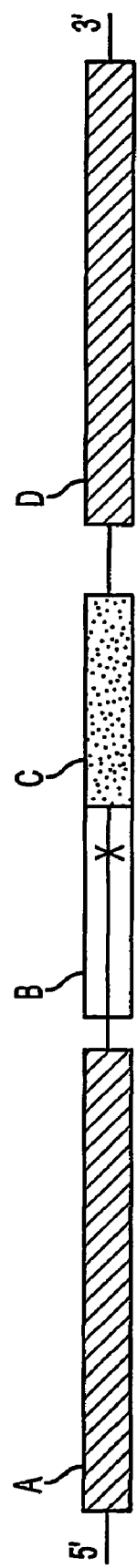
Figure 6D:
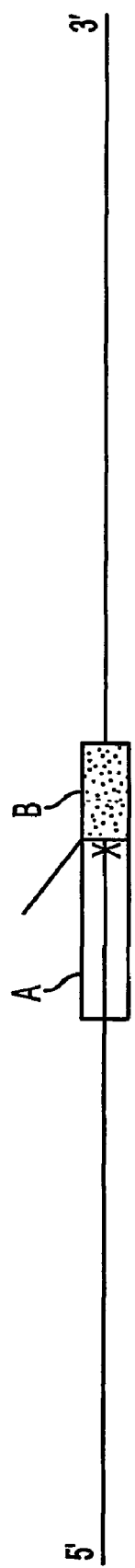
Figure 6E:
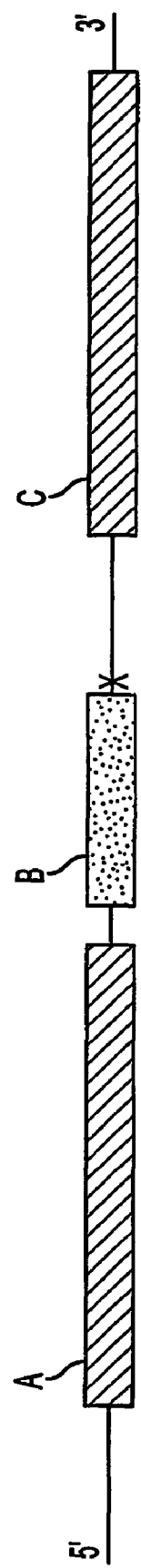
Figure 6F:
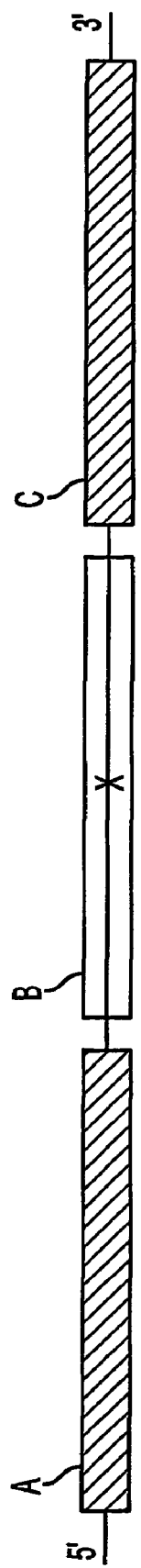
Figure 7P:
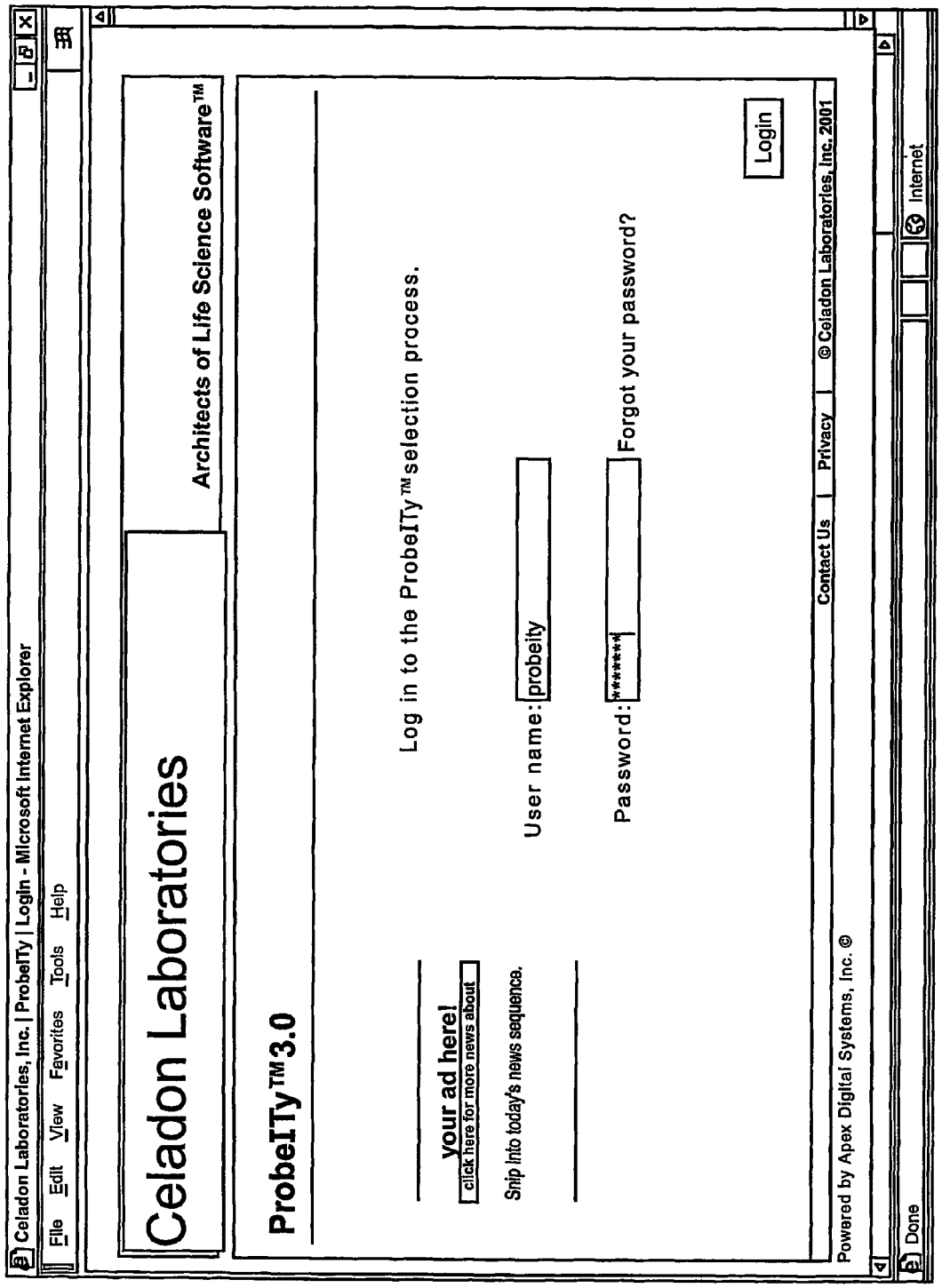
Figure 7Q:
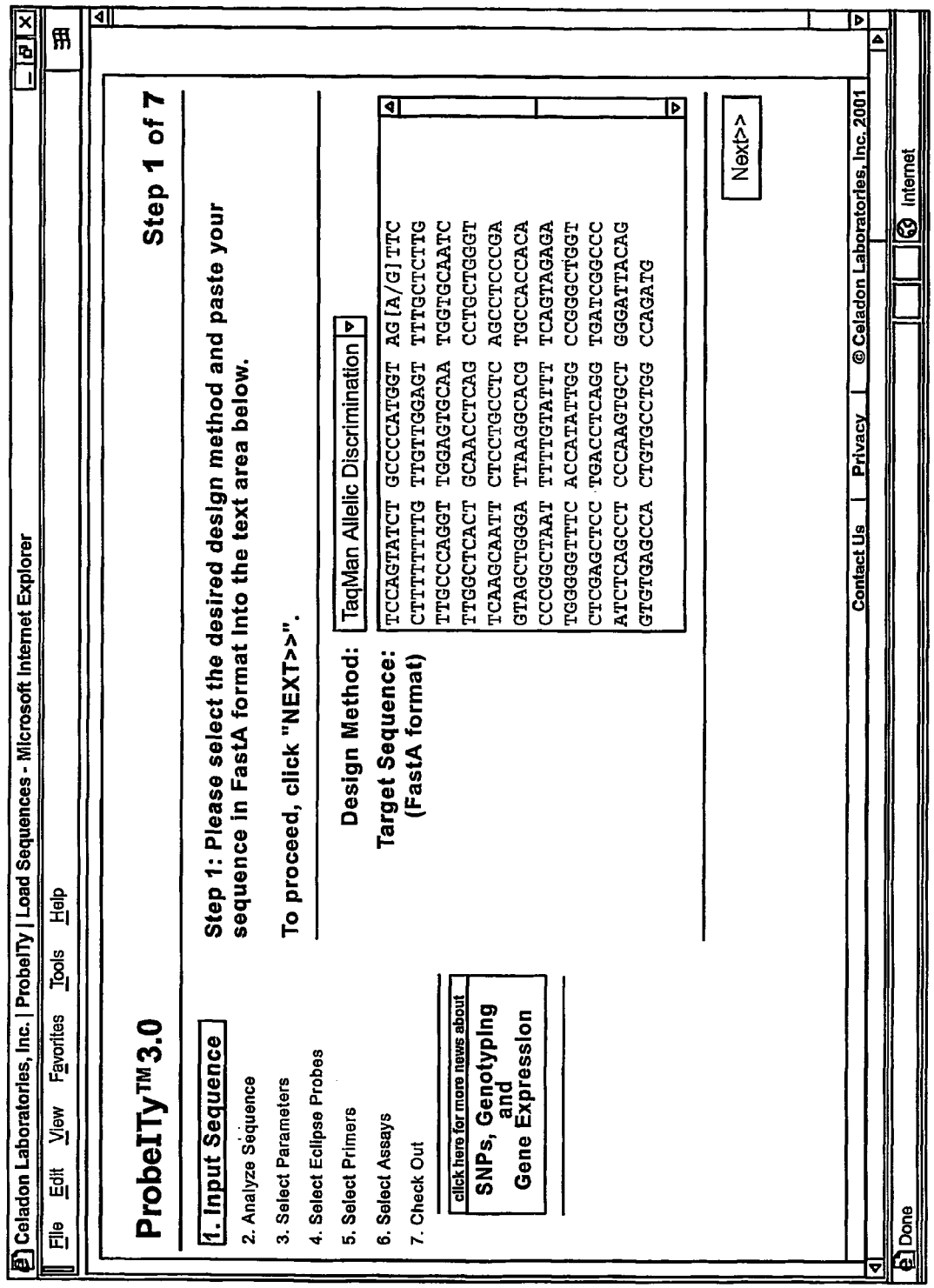
Figure 7R:
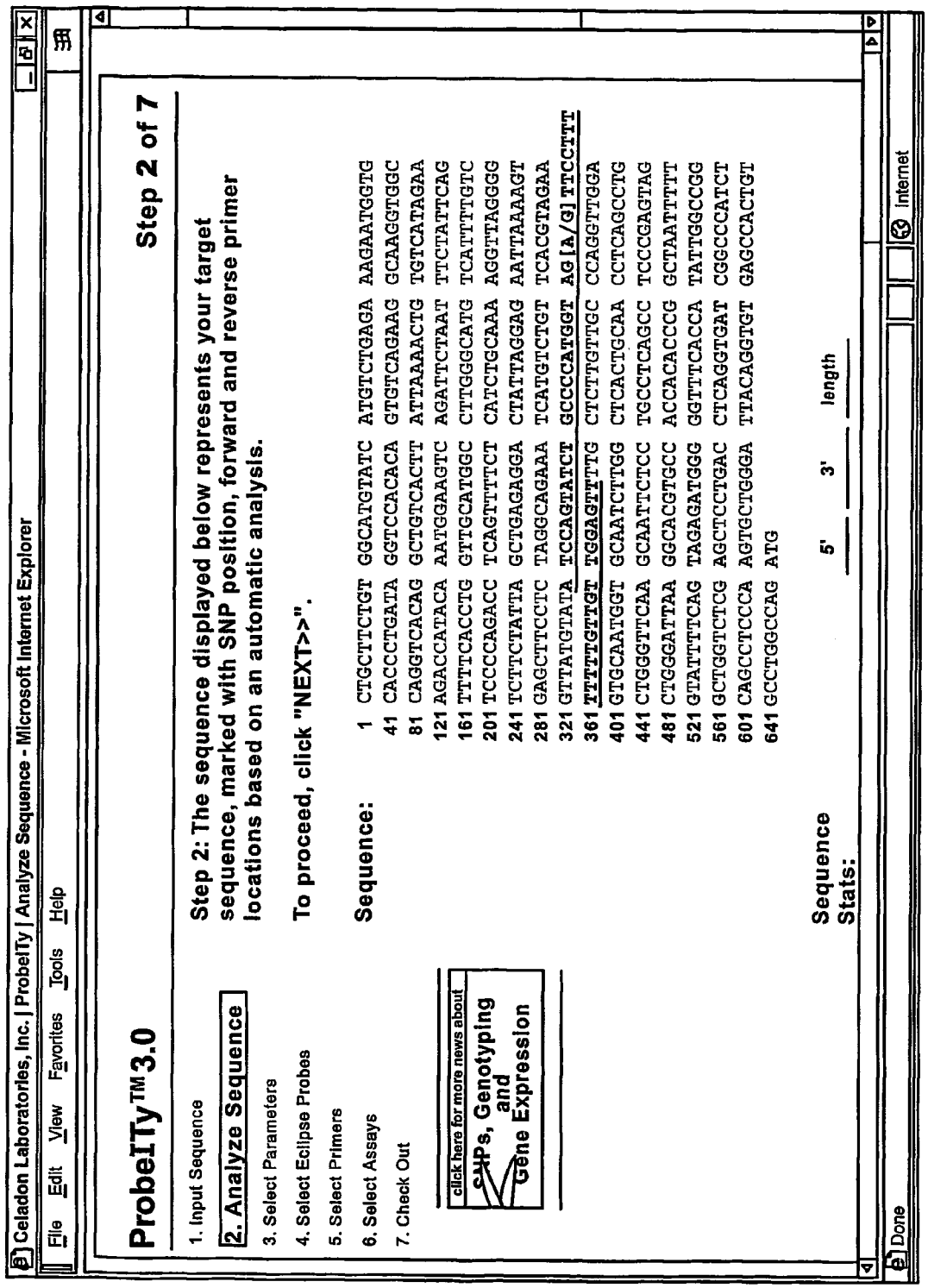
Figure 7T:
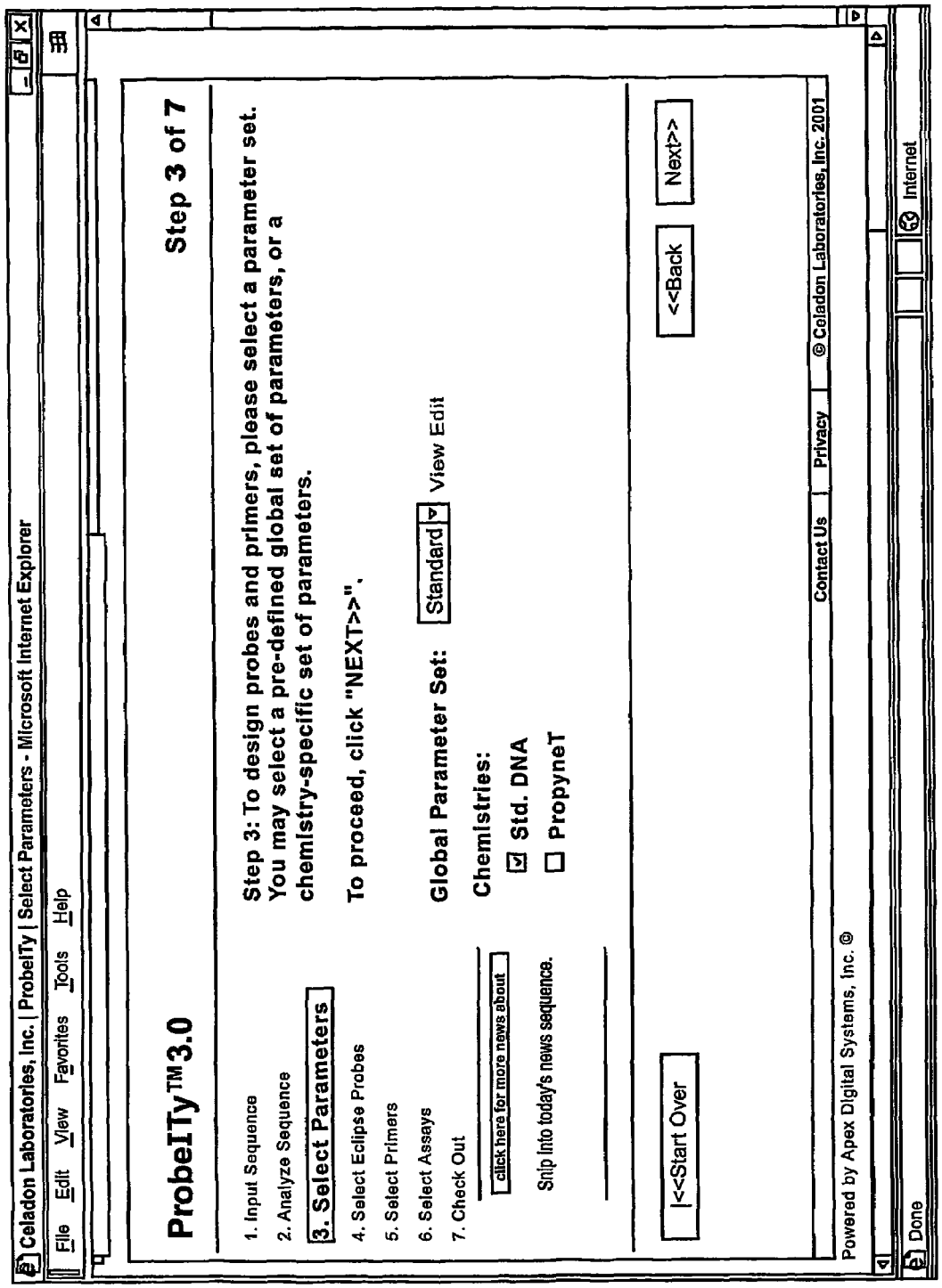
Figure 7U:
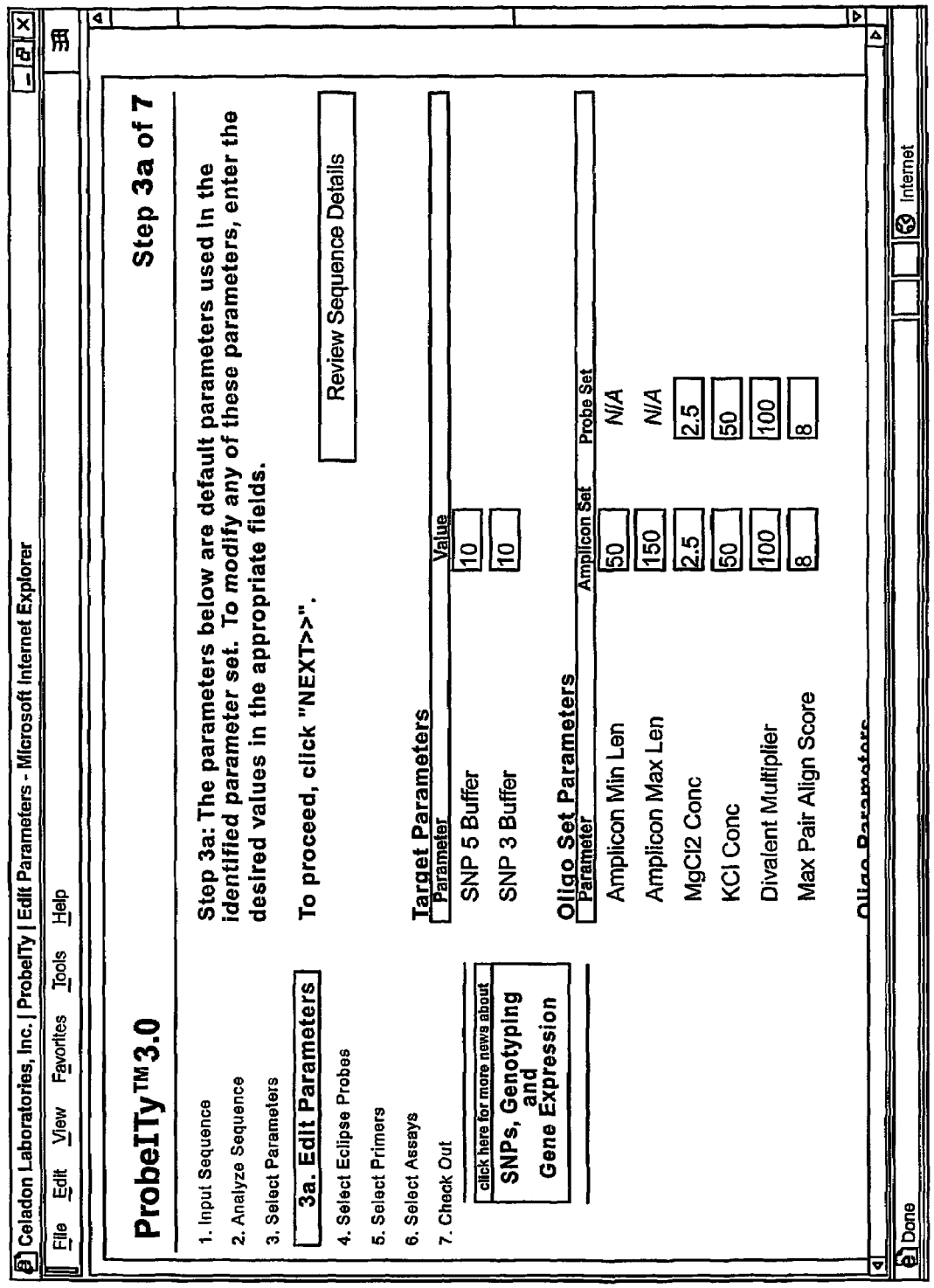
Figure 8A:
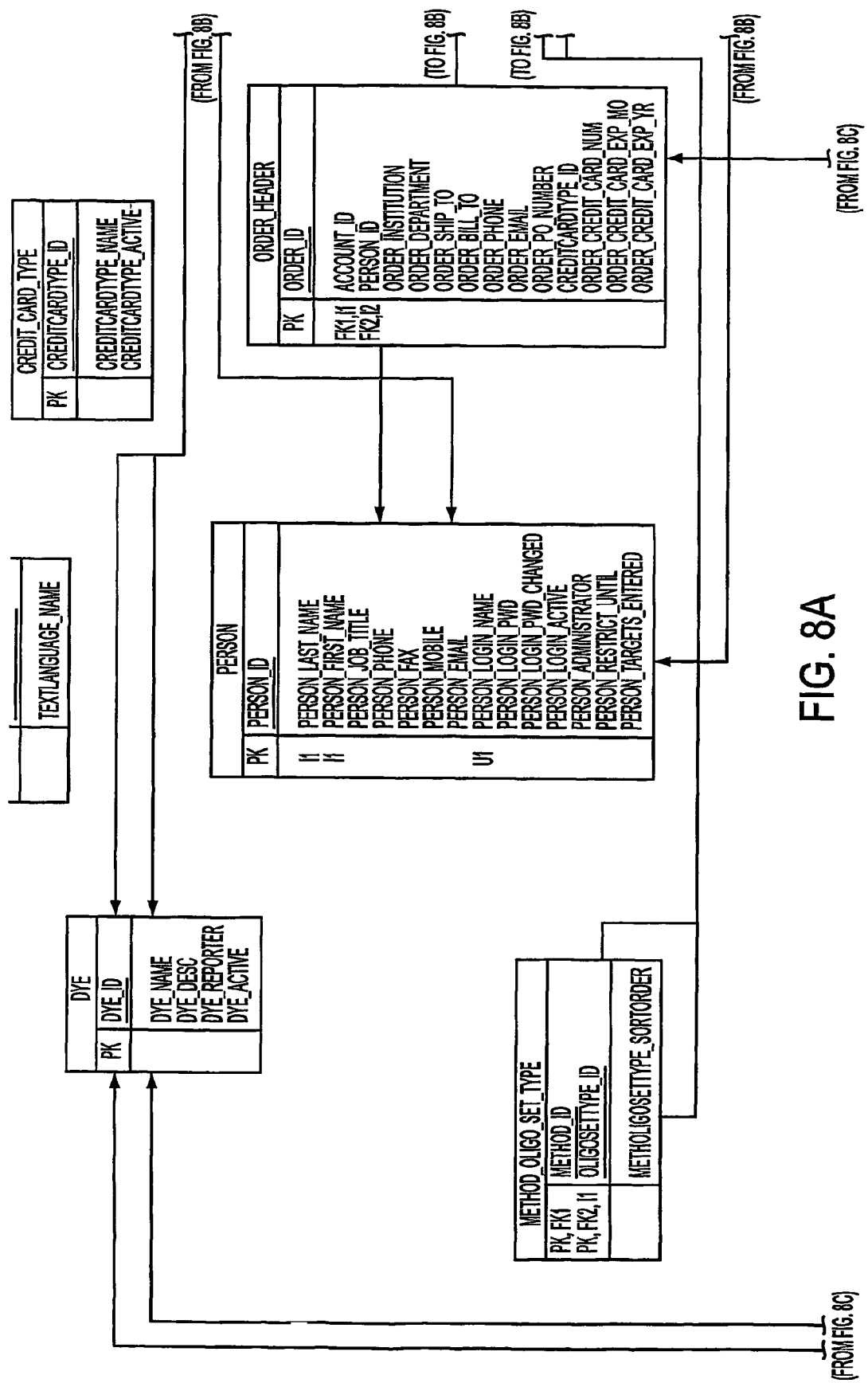
FIG. 8 shows a database of a relational database containing information such as target nucleic acid sequence data and allelic sequences thereof, target nucleic acid sequences desired as targets for hybridization or cloning, reagent oligonucleotide sequence information, the authentication information of the scientist; investigator; or user submitting or retrieving information, biochemical methods and their exclusion parameters and constraints values and ranges thereof.
Figure 8B:
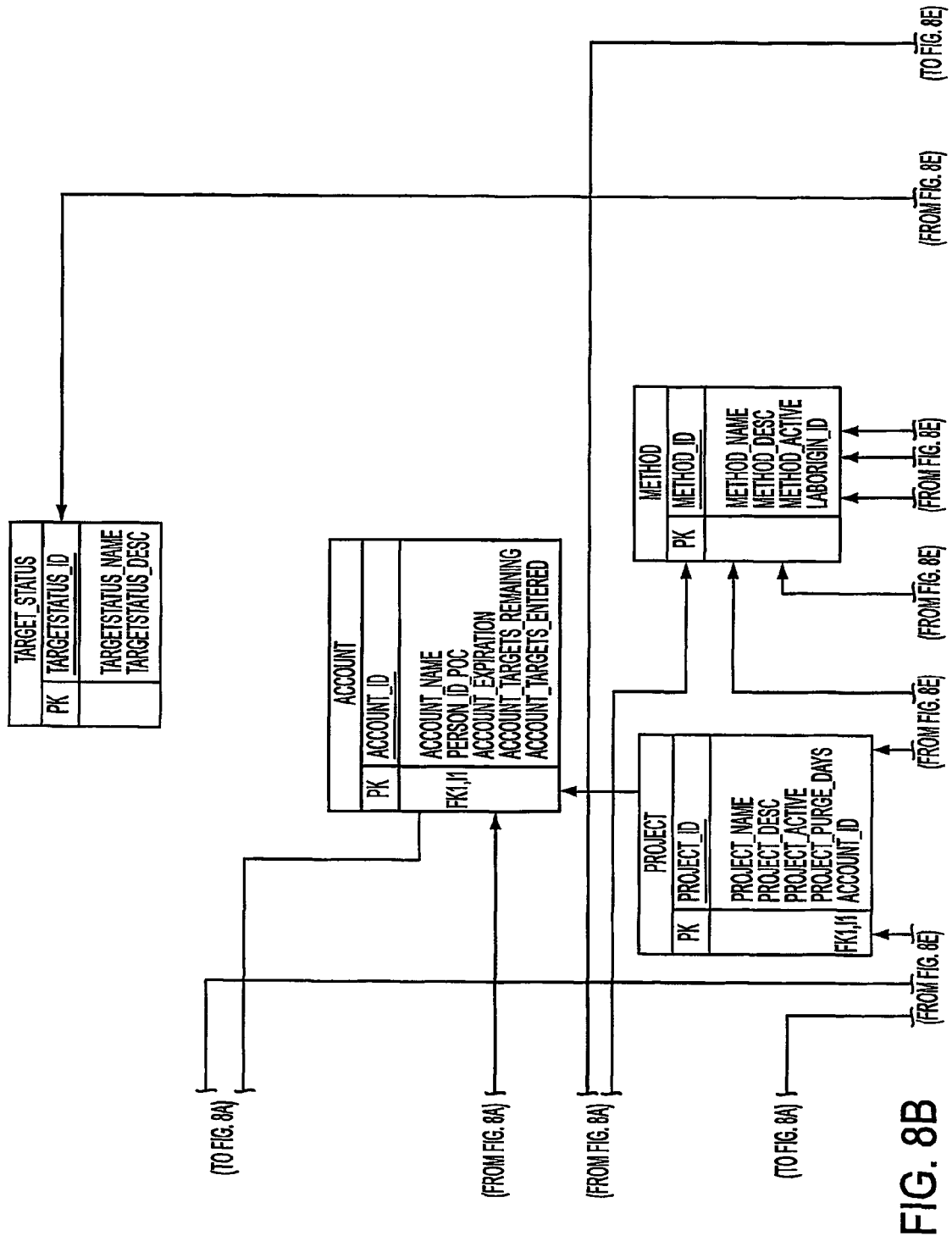
Figure 8C:
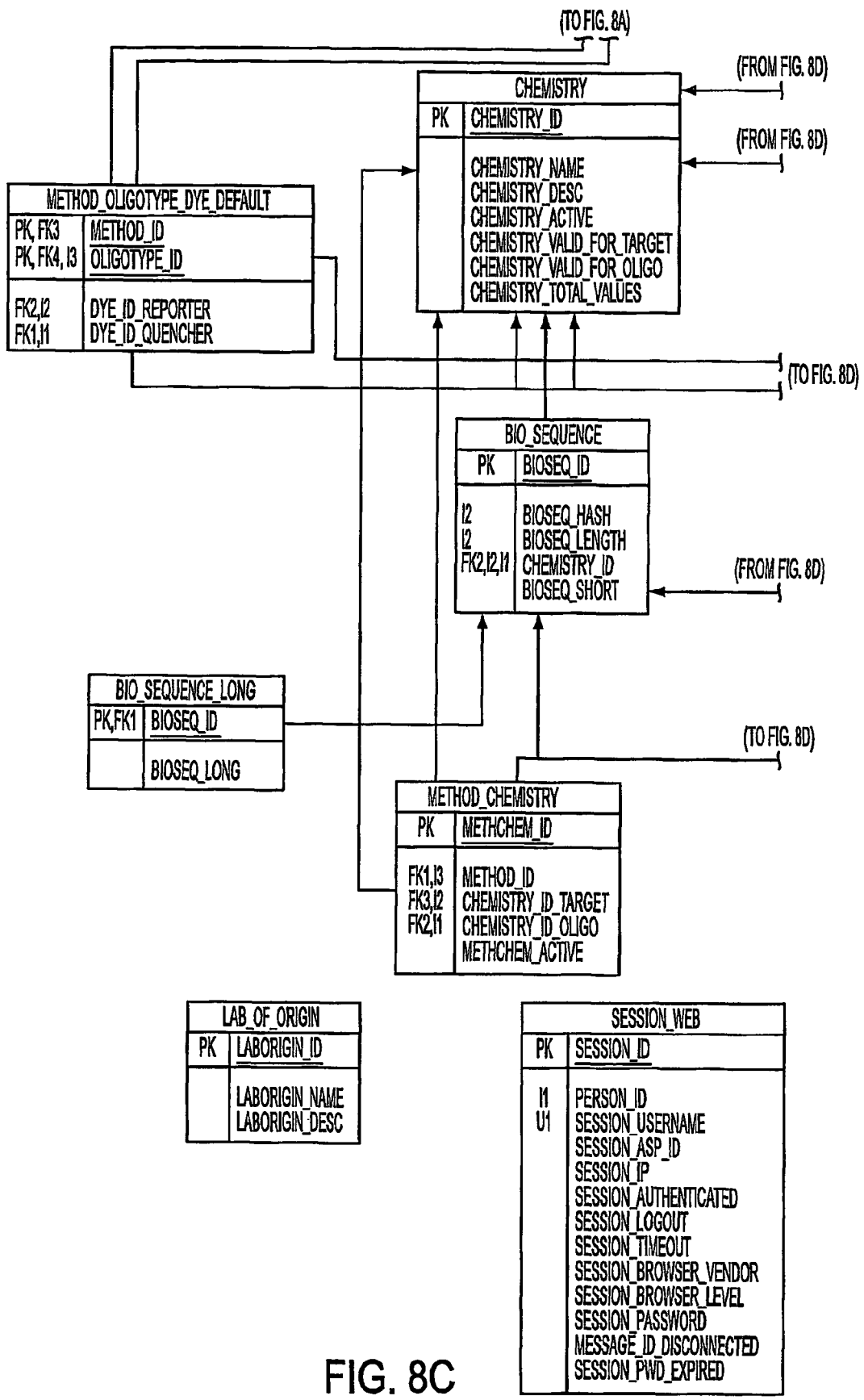
Figure 8D:
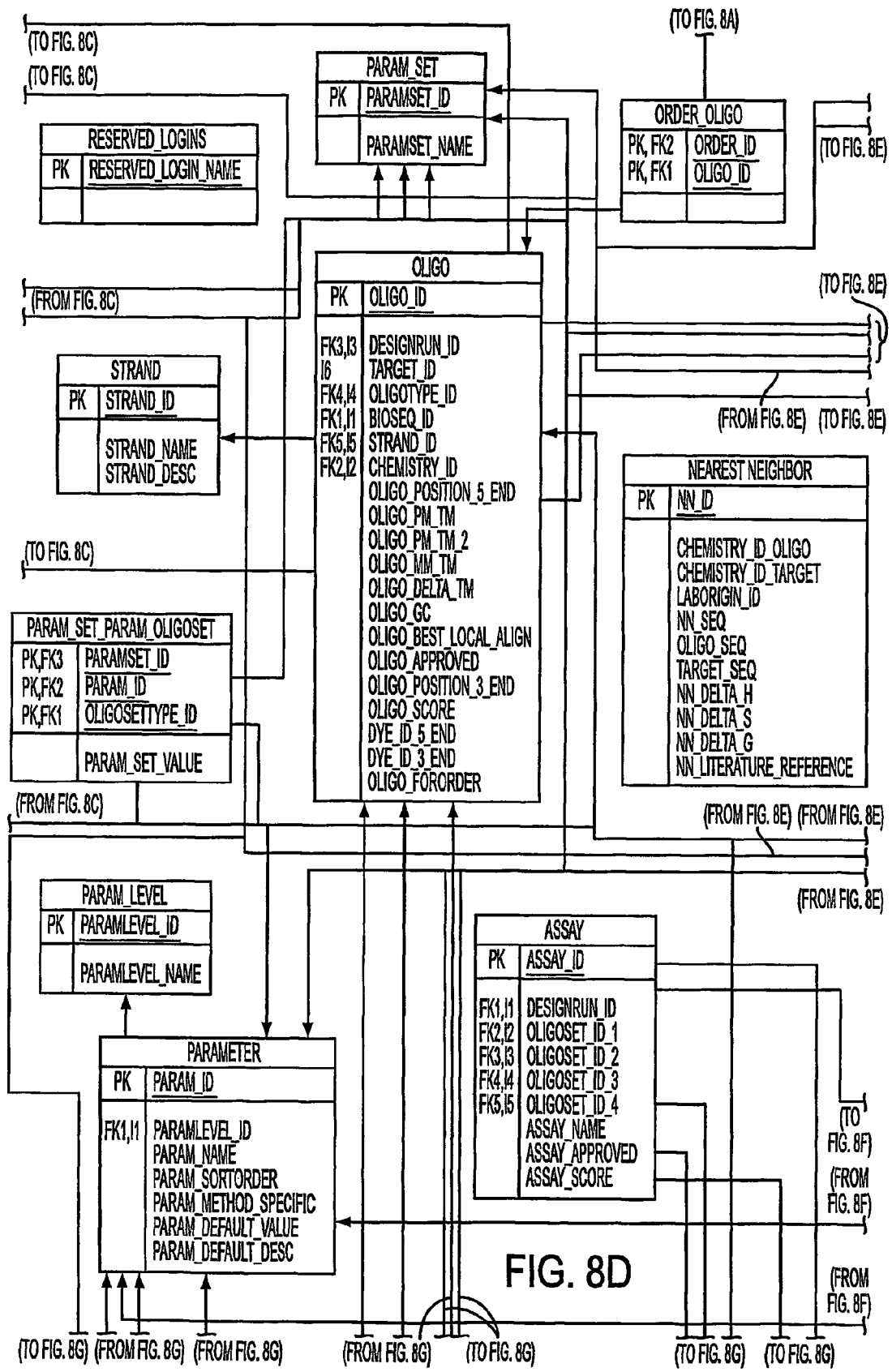
Figure 8E:
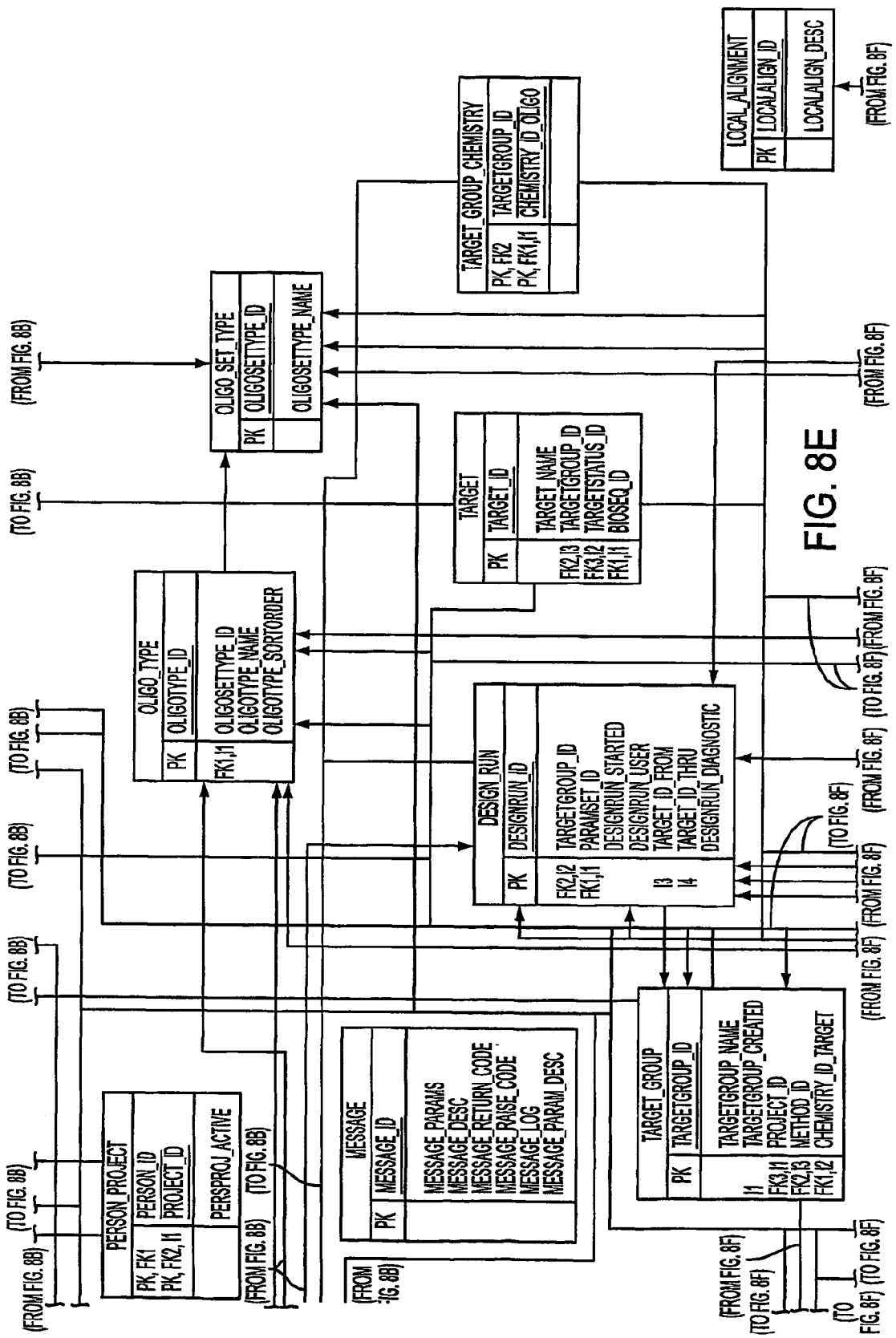
Figure 8F:
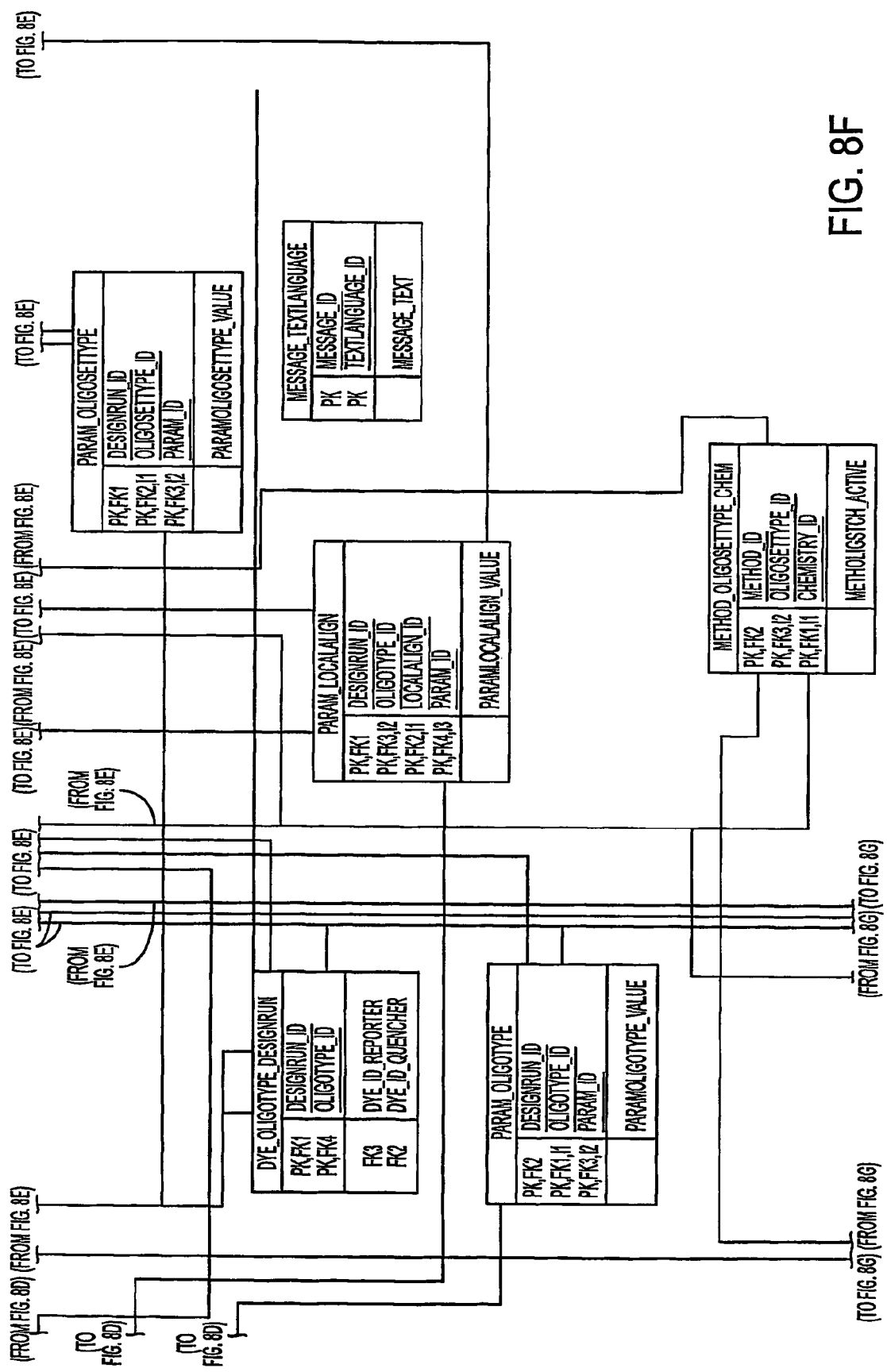
Figure 8G:
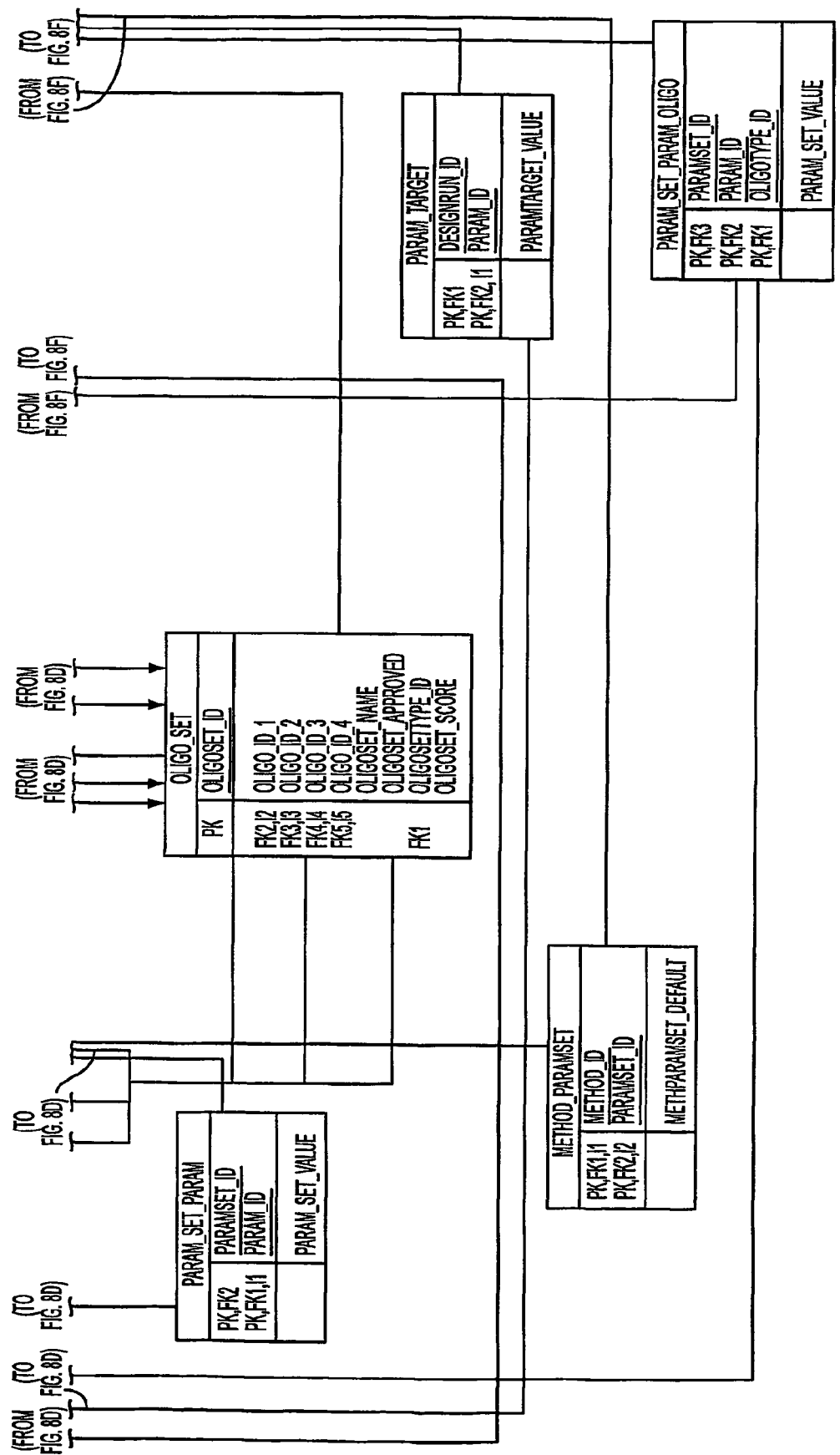

A cartoon of the examination regions and their functions for the 5' nuclease method are depicted in FIG. 6A. FIG. 6B depicts the 5' nuclease method when minor groove binder proteins are conjugated to the oligonucleotide. Minor groove binder proteins have been shown to increase $\Delta T_m$ and yield excellent allelic discrimination.

TABLE 1B

Nearest Neighbor $\Delta T_m$ Analysis of 90,000 SNPs Predicts General Applicability of 5' Nuclease Propyne T Probes

| $\Delta T_m$ | ND | 1 | 2 | 3 | 4 | 5 | 6 | 7 |
|---|---|---|---|---|---|---|---|---|
| Regular T | 17% | 2% | 14% | 29% | 22% | 11% | 4% | 1% |
| Propyne T | 0% | 0% | 1% | 10% | 32% | 40% | 15% | 2% |

The 5' nuclease method of SNP scoring exploits the difference in melting temperature $\Delta T_m$ between a probe hybridized with its perfect match complement and the same probe hybridized with a mismatch complement. To date, the general applicability of the 5' nuclease method has been limited due to the hit or miss problem of designing probes with sufficient $\Delta T_m$ to achieve robust allelic discrimination. Thermodynamic values for all possible single base mismatches are available that allow the nearest neighbor model to be applied to SNPs to predict probe $\Delta T_m$. A computer program that maximizes probe $\Delta T_m$ has been implemented and applied to 102,900 putative SNPs NCBI's dbSNP (www.ncbi.nlm.nih.gov/SNP/), release May 19, 2000). The constraints were probes with perfect match $T_m$ between 68° C. and 72° C., that have the variable position in the middle third of the probe, that do not begin with a G, and have length between 15 bp and 35 bp. Where No Data indicates no qualifying probe set, the table shows that 67% of SNPs yielded predicted $\Delta T_m$s greater than 3.0° C. using standard phosphoramadite chemistry. Three degrees is a rule-of-thumb threshold over which probes often yield discrimination. Replacement of the probe T bases with 5-propyne-2'-deoxyuridine, a T derivative, is predicted to increase $\Delta T_m$ 1.0° C. for every T in the probe. Propyne T probes have been used successfully in AT rich regions. Applying PropyneT probes for SNPs with flanking GC %<60.0 shortened the average probe from 25.0 bp to 21.5 bp, and increased the average $\Delta T_m$ 31% from 3.9° C. to 5.1° C. These results suggest that probe sets with maximal $\Delta T_m$ can be predicted, and SNPs with $\Delta T_m$ less than 3.0° C. can be avoided. Further, Propyne T probes predict success of the 5' nuclease method for all but a small fraction of SNPs.

Additional Embodiments

In addition to the 5' nuclease method, the present invention can be applied to most laboratory methods for scoring genetic diversity (FIGS. 6C-F). These include, but are not limited to, the anchor method, the Invader method, the single base extension method, pyrosequencing, ligation methods, and the DASH method. Applicable to each of these laboratory methods is the generalized method and process of defining examination regions for each oligonucleotide function, identifying the solution set by performing a comprehensive examination and evaluation of the examination regions, examining both strands, comparing solution sets from one or more biochemical models, and picking a single oligonucleotide for each function based on selection criteria.

Implied also as an additional embodiment are different kinds of genetic variations. The example and coded software addresses nucleotide substitutions. Also known as Single Nucleotide Polymorphisms, these are the substitution of one base for another. The present invention can also be employed for insertions and deletions, where one or more nucleotides are deleted or inserted in comparison to a reference sequence.

The application of the algorithm to insertions and deletions should be obvious to a practitioner of the art. Briefly, for allele-specific hybridization type methods, one hybridization probe is designed to the junction where the sequence is deleted and one hybridization probe is designed to the inserted sequence. For single base extension, the sequencing primer ends at the last base before the insertion.

As described, the invention evaluates each candidate oligonucleotide in isolation. However, the combination of oligonucleotides, one for each function, can impact assay performance. This is because there is an interaction among the oligonucleotides. Another embodiment incorporates a biochemical model in which candidate oligonucleotides for one function are evaluated with respect to candidate oligonucleotides for all other functions. Briefly, in the Overview of Process Flow Chart, FIG. 9, the box 'Apply Selection Criteria' would be enhanced to evaluate oligonucleotides among functional categories.

The following are the evaluation parameters and constraint values used by the software of the invention in a further embodiment. In this embodiment the biochemical method includes minor groove binding (MGB).

TABLE 2A

Probes - Gene Expression and DNA Detection

| | |
|---|---|
| Length | 11-18 |
| $T_m$ | 69 ± 1 |
| Max Secondary Structure $T_m$ | 35 |
| Concentration | 0.25 µM |
| MaxMonoNucRuns | 4 |
| Last5Bases | at least 3 Gs or Cs |
| Max AT run outside MGB | 3 |
| GC % | about 20% to about 80% |

TABLE 2B

Probes - SNP Discrimination

| | |
|---|---|
| Length | 11-18 |
| $T_m$ | 66 ± 2 |
| Max Secondary Structure $T_m$ | 35 |
| Concentration: | 0.25 µM |
| MaxMonoNucRuns | 4 |
| Last5Bases | at least 3 Gs or Cs |
| Max AT run outside MGB | 3 |
| GC % | about 20 to about 80 |

TABLE 2C

| Primers | |
|---|---|
| $T_m$: | 68 ± 1 |
| Max Secondary Structure $T_m$: | About 35 Celsius |
| Concentration: Left: 0.1 µM; Right: | 2.0 µM |
| MaxMonoNucRuns: | 3 |
| Avoid | A at 3' end |
| GC %: | About 40 to about 70 |
| 10 bp buffer from probe if on same strand Amplicon | |
| Max GC % | About 65 |
| Max Length | About 170 |

TABLE 2D

| Technology Platform Integration (Epoch supplies software licenses and hardware) | |
|---|---|
| Browser Compatibility | Microsoft Internet Explorer V. 4.5; Netscape Version 4.7 |
| Web Pages | Microsoft Application Server Pages Version 3.0 |
| Web Server | Microsoft IIS V 4.0 |
| Database | Oracle V. 8.7.1 |
| Analytics | Compiled DLL; Microsoft Component Object Model V |
| Operating System | Windows NT V |

Relational Database

The processing of tens of thousands of assay designs requires storing targeted variations and their flanking sequence in a database for electronic retrieval by the design software. Further, a database is needed to temporarily store and retrieve the oligonucleotides generated for each model, and to permanently store and retrieve the final oligonucleotides chosen for each design (FIG. 8).

A practitioner of the art will appreciate the power provided by the simple table layout to accommodate any genetic variation, any number of designs for a specific variation, and any number of oligonucleotides of stated function for each design.

Because typically a team of scientists conducts one or more projects, there is a Group table that records the members of the group and a Project table that can have one or more projects. Each project comprises one or more genes, and each gene typically has one or more variations. Each variation may typically have zero or more designs (Assays) for one or more methods. If an assay requires PCR, it will have a forward and reverse PCR primer that defines the PCR product, which could also be known as a Sequence Tag Site, although here no mapping information is implied. The assay will have one or more oligonucleotides, each with a stated function.

The key and foreign key fields are specified by the label key and foreign key (FK) respectively. The names of the fields typically provide enough information to a practitioner of the art to understand their meaning. Because of this self-description, the field names represent also the data dictionary.

The data tables can be populated primarily electronically. That is, genes and variable sites data can be downloaded from data warehouses. The above-described algorithm can generate Assays, PCR products and Oligos data. In the event that manual data entry is needed, also provided are a large number of Look Up Tables (LUTs), that allow users to select values from a list rather than having to type them in repeatedly.

A key feature of the tables, reflecting the present invention, is the one-to-many relationship between the Variation table and the Assay table. This allows more than one method to be applied to a particular variation, if not in the laboratory, at least at the design stage. The MethodName field in the Assay table contains this information.

Another key feature of the tables, reflecting the present invention, is the one-to-many relationship between the Assay table and the Oligos table. It is this relationship that captures the essence of the generality of the invention. In particular, the OligoUse field of the Oligonucleotide table contains the function name pertaining to the function that the oligonucleotide performs for a given method. These names include Forward PCR Primer, Reverse PCR Primer, Allele-Specific Probe, Anchor Probe, Invader Probe, etc. (see FIG. 8).

Also important to the Oligos table are the 5' modification fields and 3' modification fields. These fields contain data pertaining to modifications made to the oligonucleotide during or after synthesis, such as conjugating a fluorescent dye, a minor groove binder protein, a mass tag, or a generic sequence for signal amplification or detection.

Substantially Similar Function

A number of variations on this invention would yield identical results. For example, a described comprehensive examination method has the sequence window movement loop inside the sequence window length loop. A comparable strategy is to have the sequence window length loop inside the sequence window movement loop. Similarly, the invention is described as starting with a minimum sequence window length and incrementing towards a maximum sequence window length Starting at a maximum length and incrementing down to a minimum length is comparable. All such variations are encompassed in within the invention may employ biochemical methods as the outer loop, function as the middle loop and sequence strand as the inner loop. This means that the examination regions are separately examined for each model. However, it may be the case that two or more models share the same functions and examination regions. In such a situation it would be computationally faster to perform the comprehensive examination once and evaluate each candidate oligonucleotide multiple times, once for each model.

A feature of the tables that would be evident to a person practiced in the art is that many of the fields are annotations. Some of these fields may be eliminated to accommodate specific purposes, and many other fields included, such as all GenBank fields, as data and features are accumulated.

Operability with DNA Synthesizers

Another embodiment of the current invention is to link the underlying algorithm and computer system to a DNA synthesizer such that the reagent oligonucleotide sequences generated can be inputted into the synthesizer to make the desired probes or primers and further automate the process. DNA synthesizer software generally accepts sequence information in the form of text or ASCII, most accept sequence in a plurality of computer encoded formats. A person having ordinary skill in the art recognizes that computerized text information can be readily converted from one format to another through text filters or word processor embedded conversion software. DNA synthesizers can be made operatively linked to a computer system directly or remotely by any means known in the art (e.g., serial or parallel connectivity, SCSI, SCSI-2, Cray Cabling, Universal Serial Bus, coax cabling, fiber optic cabling, all forms of computer network connectivity, etc. . . . ). Commercially available DNA synthesizers include but are not limited to MerMade II™ (BioAutomation), Perkin Elmer/Applied Biosciences, Inc. Model 394/5 DNA Synthesizer, Labtronix DNA synthesizer, or ASM-700 DNA synthesizer (BIOSSET).

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

The following and any foregoing references and publications are herein incorporated by reference in their entirety:

Allawi H. T. & SantaLucia Jr, J. (1998) Nearest-Neighbor Thermodynamic Parameters for Internal G-A Mismatches in DNA. Biochemistry (37) 2170-2179.

Allawi H. T. & SantaLucia Jr, J. (1998) Thermodynamics of Internal C-T Mismatches in DNA. Nucleic Acids Research 26(11):2694-2701.

Allawi H. T. & SantaLucia Jr. J. (1998) Nearest-Neighbor Thermodynamics of Internal A-C Mismatches in DNA: Sequence Dependence and pH Effects. Biochemistry (37) 9435-9444.

Allawi H. T. & SantaLucia, Jr. J. (1997) Thermodynamics and NMR of Internal G-T Mismatches in DNA. Biochemistry 36:10581-10594.

Balaban D J et al. (1999) System for Providing a Polymorphism Database. WO 99/05324.

Landegren U, Nilsson M, & Kwok P-Y (1998) Reading Bits of Genetic Information: Methods for Single-Nucleotide Polymorphism Analysis. Genome Research 8:769-776.

Livak K J (1999) Allelic discrimination using the fluorescent probes and the 5' nuclease assay. Genetic Analysis: Biomolecular Engineering (14) 143-149.

Morin P. A., Saiz R. & Monjazeb A (1999) High-throughput Single Nucleotide Polymorphism Genotyping by Fluorescent 5' Exonuclease Assay. BioTechniques 27:538-552.

Peyret, N., Seneviratne, P. A., Allawi, H. T. & SantaLucia, Jr. J (1999) Nearest Neighbor Thermodynamics and NMR of DNA Sequences with Internal A-A, C-C, G-G and T-T Mismatches. Biochemistry (38) 3468-3477.

Sabatini et al. (1999) Database and Systems for Determining, Storing and Displaying Gene Locus Information. U.S. Pat. No. 5,970,500.

SantaLucia, Jr. J. (1998) A Unified View of Polymer, Dumbbell, and oligonucleotide DNA nearest-neighbor thermodynamics. Proc. Natl. Acad. Sci. (95) 1460-1465.

Yuan, C. C., Peterson R. J., Wang C-D, Goodsaid, F, Waters, D. J. (2000) 5' Nuclease Assays for the Loci CCR5-+/D32, CCR2-V64I, and SDF1-G801A Related to Pathogenesis of AIDS. Clinical Chemistry 46(1):24-30.

---

What is claimed is:

1. A computer implemented method for determining an optimal reagent oligonucleotide sequence for use in a biochemical method for evaluating a target nucleic acid sequence having a target feature, the computer implemented method comprising using a computer programmed to execute each of the following steps:
   (a) receiving a set of exclusion values and/or ranking values specific to the biochemical method,
   (b) receiving sequence windows that are within 30 kb of a target feature or encompass the target feature for both the sense and antisense strands of the target nucleic acid sequence, wherein the sequence windows have a start and a stop position,
   (c) generating candidate reagent oligonucleotide sequences complementary to one or both of the sense and antisense strands of the target nucleic acid sequence within each sequence window by moving the sequence window one base at a time from the start position to the stop position, the reagent oligonucleotide sequences having a length less than or equal to the sequence window,
   (d) evaluating the candidate reagent oligonucleotide sequences against the exclusion and/or ranking parameters, wherein candidate oligonucleotide sequences that satisfy the exclusion and/or ranking parameters are retained,
   (e) selecting at least one retained candidate oligonucleotide sequence for use in the selected biochemical method as applied to the target nucleic acid sequence and displaying the retained sequence in a graphical user interface or storing the retained sequence on a computer readable medium.

2. The method of claim 1, further comprising: receiving the target nucleic acid sequence, the sequence having at least one target feature, and receiving a selection of the biochemical method for evaluating the target nucleic acid sequence.

3. The method of claim 1, comprising evaluating candidate oligonucleotide sequences against both exclusion and ranking values.

4. The method of claim 1, comprising generating more than one type of candidate sequences and evaluating the more than one type of sequences, the evaluating comprising evaluating the candidate sequences against compatibility values, and further comprising selecting an optimal set of reagent nucleotides comprising more than one oligonucleotide sequence.

5. The method of claim 1, wherein the generating step comprises stepping the sequence window along an examination region of the target sequence.

6. The method of claim 1, wherein the generating step comprises selecting all possible reagent oligonucleotide sequences within a sequence window.

7. The method of claim 1, wherein a sequence window has a minimum length sufficient to generate candidate reagent oligonucleotides specific for the target nucleic acid sequence.

8. The method of claim 1, comprising: discarding a generated reagent oligonucleotide sequence if it falls outside the range of exclusion constraint values, and saving a generated reagent oligonucleotide sequence if it falls within the exclusion constraint values, and ranking the saved reagent oligonucleotide sequences based on comparison to one or more ranking values thereby providing several reagent oligonucleotide sequences, and selecting from the ranked reagent oligonucleotide sequences optimal reagent oligonucleotide sequences for the selected biochemical method as applied to the target nucleic acid sequence.

9. The method of claim 1 further comprising cataloguing the target nucleic acid sequences together their corresponding optimal reagent oligonucleotide sequences and the corresponding biochemical method in a computer database.

10. A computer readable data storage medium storing computer readable program code for causing a computer to perform the steps of the method in claim 9.

11. The method of claim 1 wherein at least one generated reagent oligonucleotide sequence comprises a sequence complementary to the target feature.

12. The method of claim 1 comprising receiving a plurality of biochemical methods each having evaluation parameters and having exclusion, ranking, and/or compatibility values, and further comprising generating and evaluating candidate sequences for one of the biochemical methods.

13. The method of claim 1 comprising receiving a selection of at least one reagent oligonucleotide sequence from the group consisting of a forward and reverse primer pair and one or more probes.

14. The method of claim 1 wherein the biochemical method is selected from the group consisting of: the polymerase chain reaction, propyneT chemistry, phosphoramadite chemistry, reverse transcriptase-polymerase chain, ReactionNucleotide.TM. Sequencing, the anchor method, the Invader method, the single base extension method, cycle sequencing, cyclical polymerase chain reaction, pyrosequencing, ligation, fluorescent in situ hybridization, allele-specific oligonucleotide hybridization (ASOH), dynamic allele-specific hybridization (DASH), antisense oligonucleotide chemistry, nucleic acid hybrid chemistry, and DNA/RNA repair.

15. The method of claim 1 wherein the evaluation parameters are selected from the group consisting of: OligoTm, BufferMg+, BufferK+, DivalentMultiplier, Oligonucleotide Concentration, AmpliconTm, Amplicon Length, AmpliconGC, OligoLength, OligoGC, OligoMonoNucRunLength, Oligo5EndLinker, Oligo5EndModification, Oligo5EndTail, Oligo5EndAllowedBases, Oligo5EndLeftPosition, Oligo5EndRightPosition, Oligo3EndLinker, Oligo3EndModification, Oligo3EndTail, Oligo3EndAllowedBases, Oligo3EndLeftPosition, Oligo3EndRightPosition, Oligo3EndAnalysisLength, Oligo3EndGPlusC, Oligo3 EndDeltaG, Oligo3EndGCClampLength, OligoAlignMatch, OligoAlignMisMatch, OligoAlignBulgePenalty, OligoAlignMaxBulgeAllowed, OligoHairPinMinStemLength, OligoHairPinMnLoopLength, OligoHairPinScore, OligoHairPinDeltaG, OligoHairPinTm, OligoPairAlignScore, OligoPairAlignDeltaG, OligoPairAlignTm, Oligo3EndPairAlignScore, Oligo3EndPairAlignDeltaG, Oligo3EndPairAlignTm, SequenceFeature5EndBufferLength, SequenceFeature3EndBufferLength, SequenceFeaturePosition5End, SequenceFeaturePosition3End, and Library SequenceAlignScore.

16. The method of claim 1 wherein the reagent oligonucleotides have a length between 10 and 50 base pairs.

17. The method of claim 1 wherein the reagent oligonucleotides have a $T_m$ of about 50 to about 80 degrees Celsius.

18. The method of claim 1 wherein the reagent oligonucleotides have a guanine-cytosine content between about 10% to about 90%.

19. The method of claim 1 wherein the reagent oligonucleotides have a maximum secondary structure $T_m$ of about 35 degrees Celsius.

20. The method of claim 1 wherein an exclusion value is that the reagent oligonucleotide sequence does not contain an adenine as the ultimate 3' base.

21. The method of claim 1 wherein an exclusion value is that the reagent oligonucleotide sequence does not contain a guanine as the ultimate 5' base.

22. The method of claim 1 wherein the target nucleic acid sequence is received from a database.

23. The method of claim 1 wherein the target nucleic acid sequence comprises more than one target feature.

24. The method of claim 23 wherein the method steps are repeated until optimal reagent oligonucleotide sequences have been generated for all target features and their corresponding biochemical methods.

25. The method of claim 1 wherein the target feature of the target nucleic acid sequence is selected from the group consisting of: a single nucleotide polymorphism, a multimeric subsequence of the target nucleic acid sequence, a cloning sequence, the entire target nucleic acid sequence, a codon, an exon, an intron, a telomere, a viral sequence, a transposon, a noncoding region, a promoter, an enhancer sequence, an expressed sequence tag, and a sequence tagged site.

26. The method of claim 1 wherein the reagent oligonucleotide sequence is selected from the group consisting of: an amplification primer, a sequencing primer, a sequence specific hybridization probe, an anchor probe, an invader probe, a reporter probe, and an antisense oligonucleotide.

27. A computer readable data storage medium storing computer readable program code for causing a computer to perform the steps of the method in claim 1.

28. The method of claim 1, comprising determining a first oligonucleotide prior to determining other oligonucleotides.

29. The method of claim 1, further comprising receiving target nucleic acid sequences that have multiple alleles.

30. The method of claim 1, comprising selecting oligonucleotides to at least one allele.

31. The method of claim 30, comprising selecting oligonucleotides to multiple alleles.

32. The method of claim 1, comprising selecting multiple target nucleic acid sequences per input sequence.

33. The method of claim 1, wherein the start and stop position are set in relation to the position of the target feature.

34. The method of claim 1, wherein step (b) occurs before step (c).

35. A computer system comprising: a computer having a database storing a plurality of target nucleic acid sequences having at least one target feature; a graphical user interface that permits selection of a said target nucleic acid sequence from said database, selection of a biochemical method for evaluating the selected target nucleic acid sequence and the display of reagent oligonucleotide sequences that satisfy exclusion and ranking parameters of said biochemical method; and a computer-readable data storage medium comprising program code for defining a set of exclusion values and/or ranking values specific to the biochemical method, defining sequence windows that are within 30 kb of a target feature or encompasses the target feature for both the sense and antisense strands of the target nucleic acid sequence, wherein the sequence windows have a start and a stop position, generating candidate reagent oligonucleotide sequences complementary to one or both of the sense and antisense strands of the target nucleic acid sequence within sequence window by moving the sequence window one base at a time from the start position to the stop position, the reagent oligonucleotide sequences having a length less than or equal to the sequence window, evaluating the candidate reagent oligonucleotide sequences against the exclusion and/or ranking parameters, and retaining candidate oligonucleotide sequences that satisfy the exclusion and/or ranking parameters, selecting and displaying at least one retained oligonucleotide sequence for use in the selected biochemical method as applied to the target nucleic acid sequence.

36. The computer system of claim 35, wherein the graphical user interface permits selecting from the displayed reagent oligonucleotide sequence.

37. A process of manufacturing reagent oligonucleotides comprising using reagent oligonucleotide sequences generated by the computer system of claim 35 in a nucleic acid synthesizer to produce the selected reagent oligonucleotides.

38. A kit of a predetermined number of reagent oligonucleotides optimized for a biochemical method used in evaluating a target nucleic acid sequence, the reagent oligonucleotides made by the process of claim 37.

39. The kit of claim 38 wherein the predetermined number is one or more.

40. A method of ordering a kit of reagent oligonucleotides comprising: using a computer system of claim 35, that receives the desired target nucleic acid sequence, wherein the target nucleic acid sequence has at least one target feature, generating a set of reagent oligonucleotide sequences useful in one or more biochemical methods used in evaluating said target nucleic acid sequence, receiving a selection of desired sequences from the set of generated reagent oligonucleotide sequences, outputting the received selection to a device capable of synthesizing a kit of reagent oligonucleotides based on the selected reagent oligonucleotide sequences, and providing instructions to ship said kit of reagent oligonucleotides.

41. The method of claim 40 further comprising receiving payment information into said computer system.

* * * * *